(12) United States Patent
Naghavi et al.

(10) Patent No.: US 6,451,044 B1
(45) Date of Patent: Sep. 17, 2002

(54) METHOD AND APPARATUS FOR HEATING INFLAMMED TISSUE

(75) Inventors: Morteza Naghavi, Houston, TX (US); Bujin Guo, Houston, TX (US); Birendra Lal, Houston, TX (US); S. Ward Casscells, III, Houston, TX (US); James T. Willerson, Houston, TX (US)

(73) Assignees: Board of Regents, The University of Texas System, Austin, TX (US); Texas Heart Institute, Houston, TX (US)

( * ) Notice: Subject to any disclaimer, the term of this patent is extended or adjusted under 35 U.S.C. 154(b) by 0 days.

(21) Appl. No.: 09/473,919

(22) Filed: Dec. 28, 1999

Related U.S. Application Data

(63) Continuation of application No. 09/303,313, filed on Apr. 30, 1999, which is a continuation of application No. 08/934,260, filed on Sep. 19, 1997, now Pat. No. 5,906,636.
(60) Provisional application No. 60/114,326, filed on Dec. 31, 1998, and provisional application No. 60/026,418, filed on Sep. 20, 1996.

(51) Int. Cl.$^7$ ................................................. A61N 1/00
(52) U.S. Cl. ........................................ 607/96; 623/1.42
(58) Field of Search ........................ 607/96, 100, 101; 606/32, 33; 623/1.19, 1.23, 1.42

(56) References Cited

U.S. PATENT DOCUMENTS

| | | | |
|---|---|---|---|
| 4,799,479 A | | 1/1989 | Spears |
| 4,807,620 A | | 2/1989 | Strul et al. |
| 5,053,033 A | | 10/1991 | Clarke |
| 5,057,105 A | | 10/1991 | Malone et al. |
| 5,057,106 A | | 10/1991 | Kasevich et al. |
| 5,087,256 A | | 2/1992 | Taylor et al. |
| 5,100,429 A | | 3/1992 | Srofsky et al. |
| 5,149,319 A | * | 9/1992 | Unger |
| 5,289,831 A | * | 3/1994 | Bosley |
| 5,496,271 A | | 3/1996 | Burton et al. |
| 5,591,199 A | | 1/1997 | Porter et al. |
| 5,620,438 A | | 4/1997 | Amplatz et al. |
| 5,836,896 A | | 11/1998 | Rosenschein |
| 5,849,028 A | | 12/1998 | Chen |
| 5,871,449 A | | 2/1999 | Brown |
| 5,924,997 A | | 7/1999 | Campbell |
| 5,935,075 A | | 8/1999 | Casscells et al. |
| 5,941,869 A | * | 8/1999 | Patterson et al. |

FOREIGN PATENT DOCUMENTS

| | | |
|---|---|---|
| EP | 0856278 A2 | 8/1998 |
| EP | 1025797 A1 | 8/2000 |
| WO | 8911311 A1 | 11/1989 |
| WO | 9710748 A1 | 3/1997 |

OTHER PUBLICATIONS

Barnett et al; Is Diagnostic Ultrasound Safe?; Med. Journ of Australia, vol. 160, No. 1, Jan. 3, 1994; pp. 33–37.

Barnett et al.; Biological Effects Due to Heat and the Most Thermally Sensitive Sites with Particular Reference to the Embryo and Fetus; Ultrasound in Med. & Biol., vol. 18, No. 9, pp. 739–750 (1992).

Belli e al.; Influence of Temperature on the Radiation Response of Mammalian Cells in Tissue Culture, Radiation Research, 18, 272–276 (1963).

(List continued on next page.)

*Primary Examiner*—Scott M. Getzow
(74) *Attorney, Agent, or Firm*—Oppenheimer Wolff & Donnelly LLP

(57) ABSTRACT

The present invention relates to methods for treating inflammation in body tissues. More specifically, certain disclosed methods relate to selectively inducing apoptosis in inflammatory immune cells by heating cells for a sufficient time and at a sufficient temperature to induce programmed cell death. The disclosed stents can be placed in contact with the inflammatory cells and heated under controlled conditions. The disclosed apparatus and methods are particularly suitable for treating athersclerotic plaques.

29 Claims, 7 Drawing Sheets

OTHER PUBLICATIONS

Berliner et al.; Atherosclerosis: Basic Mechanisms—Oxidation, Inflammation, and Genetics, Circulation, vol. 91, No. 9, May 1, 1995, pp. 2488–2496.

Biffl et al.; Interleukin–6 Delays Neutrophil Apoptosis, Arch Surg/vol. 131, Jan. 1996, pp. 24–30.

Blackburn et al.; The Sensitivity to Hyperthermia of Human Granulocyte/Macrophage Progenitor Cells (CFU–GM) Derived from Blood or Marrow of Normal Subjects and Patients with Chronic Granulocytic Leukemia, Br. J. Cancer (1984), 50, 745–751.

Buja et al.; Role of Inflammation in Coronary Plaque Disruption, pp. 503–505, Circulation, vol. 89, No. 1, Jan. 1994.

Casscells et al; Thermal Detection of Cellular Infiltrates In Living Atherosclerotic Plaques: Possible Implications for Plaque Rupture and Thrombosis, pp. 1447–1449, The Lancet, vol. 347, May 25, 1996.

Casscells et al.; Mechanisms of Restenosis; Texas Heart Institute Journal; vol. 21, No. 1, pp. 68–77, 1994.

Cassis et al.; Near–IR Imaging of Atheromas in Living Arterial Tissue; Ana. Chem 65:1247–56 (1993).

Chen et al.; Induction of Prostaglandin Production by Hyperthermia in Murine Peritoneal Exudate Macrophages, Cancer Research 47, 11–15, Jan. 1, 1987.

Cohen et al.; The Response of Guinea Pig Airway Epithelial Cells and Alveolar Macrophages to Environmental Stress; American Journal of Respiratory Cell and Molecular Biology, vol. 5, No. 2, Aug. 1991, pp. 133–143.

Elkon, et al.; Thermal Inactivation Energy of Granulocyte-Monocyte Stem Cells, Radiation Research 87, 368–372 (1981).

Ensor et al.; Warming Macrophages to Febrile Range Destablizes Tumor Necrosis Factor–α mRNA Without Inducing Heat Shock; (1995). Am. J. Physiol 269: C1140–C1146.

Falk et al., Coronary Plaque Disruption; Circulation, vol. 92, No. 3, Aug. 1, 1995, pp. 657–671.

Fan et al.; The Effect of Wave Reflection and Refraction At Soft Tissue Interfaces During Ultrasound Hyperthermia Treatments, J. Acoust. Soc. Am., vol. 91, No. 3, Mar. 1992; pp. 1727–1736.

Field et al.; The Relationship Between Heating Time and Temperature: Its Relevance to Clinical Hyperthermia, Radiotherapy and Oncology, 1 (1983) 179–186.

Fouqueray et al.; Heat Shock Prevents Lipopolysaccharide–Induced Tumor Necrosis Factor–α Synthesis by Rat Mononuclear Phagocytes, Eur. J. Immunol. 1992, 22:2983–2987.

Freeman et al.; The Effect of pH on Cell Lethality Induced by Hyperthermic Treatment; Cancer, 1980; 45:2291–2300.

Gerweck et al.; Influence of Nutrient on Energy Deprivation on Cellular Response to Single and Fractionated Heat Treatments, Radiation Research 99, 573–581 (1984).

Goldberg, et al.; Transluminal Radiofrequency Tissue Ablation with Use of Metallic Stents; Journal of Vascular and Interventional Radiology; Sep.–Oct. 1997, vol. 8, No. 5; pp. 835–843.

Hamilton et al.; Bleomycin Induces Apoptosis in Human Alveolar Macrophages, Am. J. Physiol 269: L318–L325, 1995.

Haveman et al.; The Role of Energy in Hyperthermia–Induced Mammalian Cell Inactivation: A Study of the Effects of Glucose Starvation and An Upcoupler of Oxidative Phosphorylation, Journal of Cellular Physiology 107:234–241 (1981).

Katsuda et al.; Immunocytochemical Analysis of Cell Activation and Proliferation in Lesions of Young Adults; Am. Jour. of Pathology; Jun. 1993, vol. 142, No. 6; pp. 1787–1793.

Kim, Young–Myeong, et al. Nitric Oxide Protects Cultured Rat Hepatocytes from Tumor Necrosis Factor–α–Induced Apoptosis by Inducing Heat Shock Protein 70 Expression, vol. 272. No. 2. Issue of Jan. 10, pp. 1402–1411, (1997).

Kimura et al; Effects of Two Ultrasound Devices and Angles of Application on the Temperature of Tissue Phantom; JOSPT, vol. 27, No. 1, Jan. 1998, pp. 27–31.

Klostergaard et al.; Hyperthermic Modulation of Respiratory Inhibition Factor–and Iron Releasing Factor–Dependent Macrophage Murine Tumor Cytotoxicity; Cancer Research; vol. 49, No. 22, pp. 6252–6257.

Kobayashi et al.; Cell Cycle–Dependent Heat Sensitization of Murine Granulocyte–Macrophage Progenitor Cells in Regenerating Marrow, Cancer Research 45, 1459–1463, Apr. 1985.

Kunkel et al.; Regulation of Macrophage Tumor Necrosis Factor Production by Prostaglandin $E_2$, Biochemical and Biophysical Research Communication, vol. 137, No. 1., May 29, 1986, pp. 404–410.

Kwok et al.; Self–Assembled Molecular Structures as Ultrasonically–Responsive Barrier Membranes for Pulsatile Drug Delivery; Journal of Biomedical Materials Research; Nov. 2001, vol. 57, No. 2, pp. 151–164.

Lavie et al.; Age–Related Alterations in Superoxide Anion Generation in Mouse Peritoneal Macrophages Studied by Repeated Stimulations and Heat Shock Treatment; Jour. of Cellular Physiology, 152:382–388 (1992).

Luo et al; Enhancement of Thrombolysis In Vivo Without Skin and Soft Tissue Damage by Transcutaneous Ultrasound; Thrombosis Research 89 (1998) pp. 171–177.

Mangan; Lipopolysaccharide, Tumor Necrosis Factor–α, and IL–1β Prevent Programmed Cell Death (Apoptosis) in Human Peripheral Blood Monocytes, The Journal of Immunology, vol. 146, 1541–1546, No. 5, Mar. 1, 1991.

McDiarmid et al; Clinical Applications of Therapeutic Ultrasound; Physiotherapy, Apr. 1987, vol. 73, No. 4, 155–162 (1987).

Morange et al.; Interferon Pretreatment Lowers the Threshold for Maximal Heat–Shock Response in Mouse Cells, Journal of Cellular Physiology, 127:417–422 (1986).

Moreno et al.; Macrophage Infiltration Predicts Restenosis After Coronary Intervention in Patients With Unstable Angina; Circulation, 1996: 94:3098–3102.

Nagata et al.; The Fas Death Factor, Science, vol. 267, Mar. 10, 1995, pp. 1449–1456.

Nishina et al.; Stress Signalling Kinase Sek 1 Protects Thymocytes From Apoptosis Mediated by CD95 and CD3, Nature, vol. 385, Jan. 23, 1997, pp. 350–353.

Oesterle et al; The Stent Decade: 1987 to 1997; Am. Heart Journal; vol. 136, No. 4, Part 1, pp. 578–599 (1998).

O'Hara et al., Intrinsic Thermal Response, Thermotolerance Development and Stepdown Heating In Murine Bone Marrow Progenitor Cells; Int'l Jour. of Hyperthermia; vol. 8, No. 4, Jul.–Aug. 1932; pp. 451–461.

Papadimitriou et al.; Quantitative Investigations of Apoptosis of Murine Mononuclear Phagocytes During Mild Hyperthermia, Experimental and Molecular Pathology 59, 1–12 (1993).

Pizurki et al.; cAMP Modulates Stress Protein Synthesis in Human Monocytes, Macrophages, Journal of Cellular Physiology, 161:169–177 (1994).

Prins et al.; Apoptosis of Human Adipocytes in Vitro, Biochemical and Biophysical Research Communications, vol. 201, No. 2, (1994), pp. 500–507.

Raaphorst et al; Sensitivity to Heat, Radiation and Heat Plus Radiation of Chinese Hamster Cells Synchronized by Mitotic Selection, Thymidine Block or Hydroxyurea Block; J. Therm. Biol., vol. 10, No. 3, pp. 177–181, 1985.

Reddy et al.; Heat Shock Treatment of Macrophages Causes Increased Release of Superoxide Anion, Infection and Immunity, Jun. 1992, vol. 60, No. 6, pp. 2386–2390.

Ribeiro et al.; Effects of the Stress Response in Septic Rats and LPS–Stimulated Alveolar Macrophages: Evidence for TNF–α Posttranslational Regulation, Am J Respir Crit Care Med 1996: 154: 1843–1847.

Robertson et al.; Subaqueous Ultrasound: 45kHz and 1MHz Machines Compared; Arch Phys. Med. Rehabil., vol. 76, Jun. 1995, pp. 569–575.

Ross; The Pathogenesis of Atherosclerosis: A Perspective for the 1990s; Nature, vol. 362, No. 6423, Apr. 29, 1993; pp. 801–809.

Sivo et al.; Heat Shock Mimics Glucocorticoid Effects on IFN–γ–Induced FcγRI and Ia Messenger RNA Expression in Mouse Peritoneal Macrophages, The Journal of Immunology, 1996, pp. 3450–3454.

Snyder et al. Transcriptional Inhibition of Endotozin–Induced Monokine Synthesis Following Heat Shock in Murine Peritoneal Macrophages, Journal of Leukoctye Biology, vol. 51, Feb. 1992, pp. 181–187.

Steller; Mechanisms and Genes of Cellular Suicide; Science; vol. 267, Mar. 10, 1995; pp. 1445–1449.

Thompson; Apoptosis In the Pathogenesis and Treatment of Disease, Science, vol. 267, Mar. 10, 1995, pp. 1456–1462.

Topol et al.; Frontiers in Interventional Cardiology, Circulation, Journal of the American Heart Association; 1998; pp.: 1802–1820.

Vaux et al. The Molecular Biology of Apoptosis, Proc. Natl. Acad. Sci. USA, vol. 93, Mar. 1996, pp. 2239–2244.

Verheji et al.; Requirement for Cereamide–Initiated SAPK/JNK Signalling in Stress–Induced Apoptosis, Nature, vol. 380, Mar. 1996, pp. 75–79.

Wang et al.; Induction of Heat Shock Protein 72 Prevents Neutrophil–Mediated Human Endothelial Cell Necrosis; Arch Surg/vol. 130, Dec. 1995, pp. 1260–1265.

Wang et al.; Induction of Human Endothelial Cell Apoptosis Requires Both Heat Shock and Oxidative Stress Responses, Am. J. Physiol. 272, 1997, pp. C1543–C1551.

Westra et al.; Variation in Sensitivity to Heat Shock During the Cell–Cycle of Chinese Hamster Cells In Vitro, Int. J. Radiat. Biol.; 1971, vol. 19, No. 5, pp. 467–477.

Whelan et al.; Biocompatibility of Phosphorylcholine Coated Stents In Normal Porcine Coronary Arteries; Heart, Mar. 2000, vol. 83, No. 3, pp. 338–345.

Wike–Holley et al.; The Relevance of Tumour pH to the Treatment of Malignant Disease; Radiotherapy and Oncology, 2 (1984) 343–366.

Williams, Production and Transmission of Ultrasound; J. Acoust. Soc. of Physiotherapy, vol. 100, No. 4, Pt. 1, Oct. 1996, pp. 113–116.

* cited by examiner

METHOD AND APPARATUS FOR HEATING INFLAMMED TISSUE

CROSS-REFERENCE TO RELATED APPLICATION

The present application claims the benefit of 35 U.S.C. 111(b) Provisional application Ser. No. 60/114,326 filed Dec. 31, 1998, and entitled Ultrasonically Heated Stent. The present application is also a continuation to patent application Ser. No. 09/303,313 filed on Apr. 30, 1999, entitled Heat Treatment of Inflammed Tissue which is a continuation of Ser. No. 08/934,260, filed on Sep. 9, 1997, now U.S. Pat. No. 5,906,636 which claims benefit of U.S. provisional apllication No. 60/026,418 filed Sep. 20, 1996.

STATEMENT REGARDING FEDERALLY SPONSORED RESEARCH OR DEVELOPMENT

Not applicable.

BACKGROUND OF THE INVENTION

1. Field of the Invention

The present invention generally relates to methods for treating inflammed tissue. More particularly, the invention relates to stents for treating vessels and other annular organs that are capable of being selectively heated by an external source of radiation and of transferring that heat to surrounding tissue. The invention also relates to methods of making and using such heating stents to apply low-level heat to inflammed tissue

2. Description of Related Art

Coronary artery disease is a leading cause of death in industrialized countries. It is manifested by athersclerotic plaques, which are thickened areas in vessel walls. A plaque is an accumulation of cholesterol, proliferating smooth muscle cells and inflammatory cells covered by cellular secretions of collagen that form a cap over the plaque in the vessel wall. Macrophages migrate into and accumulate in a plaque causing inflammation. Inflamed plaques are most susceptible to ruptures and the formation of blood clots. Falk, E. (1995).

Atherosclerotic plaques are thought to develop in response to irritation or biochemical damage of the endothelial cells that line blood vessel walls. Agents that are known to damage these cells include cigarette smoke, high serum cholesterol (especially in the form of oxidized low density lipoprotein), hemodynamic alterations (such as those found at vessel branch points), some viruses (herpes simplex, cytomegalovirus) or bacteria (e.g., Chlamydia), hypertension, and some plasma hormones (including angiotensisn II, norepinephrine) and homocysteine. Atherosclerotic plaques grow slowly over many years in response to the cumulative injury of endothelial cells. Ross (1993), Berliner (1995).

Typically, several dozen plaques are found in arteries afflicted with this disease. It is the rupture of these plaques that brings about the terminal stage of the disease. The rupture causes a large thrombus (blood clot) to form on the inside of the artery, which may completely occlude the blood flow through the artery, thereby injuring the heart or brain. Falk, E. (1995).

In most cases of terminal coronary artery disease, only one of several plaques ruptures. Rupture typically is caused by inflammatory cells, primarily macrophages, that lay beneath the surface collagen layer of the plaques. These cells release enzymes that tend to degrade the cap. Once a plaque ruptures, blood clots are formed and it is these clots that are believed to be responsible for over one half of all heart attacks and stokes. Falk, E. (1995); Buja (1994).

Techniques have been developed to identify those plaques that are most likely to rupture because of inflammation. See U.S. patent application Ser. No. 08/717,449, which is specifically incorporated by reference herein. The most common treatment for these plaques is percutaneous transluminal coronary angioplasty (PTCA), e.g., balloon angioplasty. Frequently, however, injury to the vessel wall and disruption of the plaque core occur during restoration of vessel patency. The rapid proliferation of smooth muscle cells in response to damage and inflammation induced in the intimal and medial layers of the vessel wall occurs as part of the body's attempt to heal the "wound" to the vessel. This leads to neointimization and remodeling of the vessel wall and restenosis. Restenosis is defined as the reclosure of a previously stenosed and subsequently dilated peripheral or coronary vessel. Blood clots may form as a result of the spillage of plaque contents and due to triggering of the natural clot-forming cascade of the blood, further contributing to restenosis at the treatment site. Within weeks to months after PTCA, many individuals develop restenosis at the angioplasty site. Various approaches to balloon catheter angioplasty have been introduced, however each has failed at preventing post-angioplasty restenosis. Some of these include atherectomy devices, laser and thermal ablative devices and stents, examples of which are well known by those working in the field.

Apoptosis

It is clear that in many cases balloon angioplasty causes cellular injury and only temporarily eliminates the danger from an inflamed plaque until the advent of a secondary inflammatory response. Casscells (1994).

It has been shown that macrophages have a life span of only about a week or two in the vessel wall. Katsuda (1993). Typically, monocytes enter the atherosclerotic plaque, divide once, and contribute to plaque development by their ability to oxidize low density lipoprotein cholesterol and to release factors which cause smooth muscle proliferation and angiogenesis. The cells then undergo apoptosis, which is an active process of programmed cell death. This process differs from necrosis in that apoptosis requires the expenditure of energy, and the synthesis of new RNA and proteins in all but the inflammatory cells, the active cleavage of DNA and the shrinkage and involution of the cell with very little inflammation. Steller (1995); Nagata (1995); Thompson (1995); Vaux (1996).

Apoptosis is a form of programmed cell death in which the dying cells retain membrane integrity and are rapidly phagocytosed and digested by macrophages or by neighboring cells. It occurs by means of an intrinsic cellular suicide program that results in DNA fragmentation and nuclear and cytoplasmic condensation. The dead cells are rapidly cleared without leaking their contents and therefore little inflammatory reaction follows. It can be induced by the withdrawal of growth factors and to some extent by factors which can also cause necrosis such as extreme lack of oxygen or glucose, heat, oxidation and other physical factors.

Previously no method was known for selectively inducing apoptosis in macrophages or other inflammatory cells in a blood vessel without also inducing apoptosis in beneficial endothelial cells. Known methods for inducing apoptosis were systemic, including treatments with chemicals and elevated temperatures. Such methods are not useful as therapeutic methods because of the risk that apoptosis will develop in healthy tissue.

A number of studies have shown that heat can induce programmed cell death. Kunkel (1986) have found that indomethacin inhibits macrophage synthesis of prostaglandin but enhances macrophage production of TNF-I, which suggests that heating may have advantages over indomethacin as an anti-inflammatory treatment. Preventing the synthesis of prostaglandin, which serve as feedback inhibitors of macrophage function, limits the anti-inflammatory utility of indomethacin and presumably other inhibitors of cyclooxygenase. Field and Morris (1983) surveyed many cell types and found that the time needed to kill cells at 43° C. varied from four minutes in mouse testis, to 32 minutes in rat tumor in vivo, to 37 minutes for mouse jejunum, to 75 minutes for rat skin, 210 minutes for mouse skin and 850 minutes for pig skin. Numerous other cell types were also studied. They observed that, above 42.5° C., an increase of 1° C. produces a similar effect as doubling the duration of heat exposure. Wike-Hooly (1984) found that a low pH enhanced hyperthermic cell killing, as did a low glucose or insulin exposure and that nitroprusside also increased the cell mortality caused by hyperthermia. Raaphorst (1985) and Belli (1988) studied Chinese hamster lung fibroblasts and found that 45° C. heat and radiation were synergistic in cell killing. Raaphorst (1985) also found S-phase to be heat-sensitive and least radiosensitive, while in G1 and G2 the opposite was true. Klostergard (1989) found that cytotoxicity of macrophages was decreased by heating to 40.5° C. for 60 minutes. Westra and Dewey (1971) found that in CHO cells S phase was more sensitive to heating to 45.5° C. than was G1 phase. M phase was intermediate. In contrast, radiation killed cells preferentially in phases G1 and M1. Fifty percent of asynchronous (cycling) CHO cells were killed by a 20 minute heat treatment at 43.5° C. Freeman (1980) found that the sensitivity of CHO cells to 41° C. to 45.5° C. was increased with acidosis and that thermotolerance was induced by exposure to 42° C. for 250 minutes. Haverman and Hahn (1982) used an inhibitor of oxidative phosphorylation and found that CHO cells were thereby more prone to heat-induced death using 43° C. for one hour. Preheating, however, led to tolerance. These experiments could not determine whether hyperthermia increased ATP utilization or inhibited its synthesis. Gerweck (1984) found that CHO cells were more easily killed by 44° C. (20% died after a 15-minute exposure) when ATP was depleted by hypoxia and hypoglycemia, but neither condition alone had an effect. Lavie (1992) found that peritoneal macrophages from older mice tend to die at 42.5° C. for 20 minutes but not macrophages from younger mice. Papdimitriou (1993) found that most peritoneal murine macrophages undergo apoptosis with a five-hour exposure to 41° C., but few entered apoptosis at 30° C. Most circulating monocytes did not undergo apoptosis at 41° C., with a five-hour exposure. Mangan (1991) reported that TNF alpha and interleukin-1 beta prevent macrophage apoptosis. Chen (1987) reported that heat in the range of 41° C. to 43° C. stimulated macrophage production of prostaglandins. Prostaglandins serve to suppress macrophage production and phagocytosis. Heat did not decrease prostaglandin release from tumor cell line or from fibroblasts. They found that macrophage death began at 41° C. with a four-hour exposure. A six-hour exposure to 43° C. killed half the macrophages. Ensor (1995) found no macrophage cell death after six hours at 40° C., (vs. 37° C.) but at 43° C. only 4% of cells were viable at six hours. O'Hara (1992) found that bone marrow macrophages survive 15 minutes at 45° C. if they have been preheated for 110 minutes to 42.5° C.

Fouqueray (1992) found that exposing rat peritoneal macrophages to 39° C. to 41° C. for 20 minutes decreased synthesis of IL-1 and TNF-I. Circulating monocytes were less sensitive to heat than glomerular or peritoneal macrophages. This degree of heating did not kill the macrophages. Hamilton (1995) found that the cancer drug bleomycin blocked expression of HSP-72 in human alveolar macrophages in response to exposure to 39.8° C. This was a relatively specific effect since there was no change in overall protein synthesis and, moreover, the effect appeared to be post-transcriptional, since there was no change in mRNA levels for HSP-72. The bleomycin exposure did not cause much necrosis, but it caused marked DNA fragmentation characteristic of apoptosis. Wang (1995) found that induction of HSP-72 prevented necrosis in human endothelial cells exposed to activated neutrophils. The activated neutrophils caused necrosis of endothelial cells that had been exposed to 30 to 60 minutes of heat shock at 42° C., an exposure which by itself did not induce necrosis or apoptosis. Wang (1997) found that endothelial cells did not go to apoptosis with a 45-minute exposure to 42° C. or with exposure to TNF-I, but exposure to both did trigger apoptosis. TNF-I resulted in generation of reactive oxygen species, which the authors believe may be required, together with heat shock, to induce apoptosis in endothelial cells. Kim (1997) found that nitric oxide protected cultured rat hepatocytes from TNF-I induced apoptosis by means of inducing HSP-70. Belli (1963) observed that heating enhances cell susceptibility to radiation killing.

Cytokines are also known to influence apoptosis in macrophages and other leukocytes. William (1996) found that apoptosis in neutrophils was promoted by heat, TNF-I, or endotoxin but inhibited by LPS, GMCSF and IL-2. Biffl (1996) found that IL-6 also delayed neutrophil apoptosis. Prins (1994) found in human fat tissue explants adipocytes underwent apoptosis within 24 hours of a 60-minute exposure to 430 C. and then underwent phagocytosis, suggesting that at least some macrophages survived longer than some adipocytes. O'Hara (1992) showed that granulocyte-macrophage precursors take longer ($T_{1/2}$=36 min.) to become heat-tolerant than do stem cells or erythrocyte precursors from bone marrow. Verhelj (1996) found that 50 percent of confluent, nondividing, bovine aortic endothelial cells underwent apoptosis by 12 hours at 43° C., versus 41° C. for dividing human monoblastic leukemia of the U937 line, but this difference could well be attributable to the difference in age of the cells, cycling rate or species. D. Elkon and H. E. McGrath (1981) presented some evidence that granulocyte monocyte stem cells do not take as long as other cells to be killed at a temperature of 42.5° C. Blackburn (1984) reported that circulating monocyte precursors are more sensitive to heat than are those from bone marrow. Kobayashi (1985) reported that granulocyte-macrophage progenitor cells were more sensitive to 60 minutes at 42° C. when the marrow was regenerating (during cell division) than when it was stationary, but this is a finding in all cell types. Cohen (1991) found no difference in heat tolerance of epithelial cells and airway macrophages, as measured by immediate release of LDH and chromium-51.

A number of studies have examined the relationship between heat shock and cell killing. Nishina (1997) found that the stress-activated protein kinases (also known as the Jun N-terminal kinases) are activated in response to heat shock and other cell stresses. A knockout of one of these genes (SEK-1) resulted in fewer CD4+, CD8+ thymocytes. Pizurki and Polla (1994) found that cAMP increased synthesis of heat-shock proteins in heated macrophages. Reddy (1982) found that heat shock of murine macrophages increased their production of superoxide but did not change their production of hydrogen peroxide or their microbicidal activity. Sivo (1996) found that heat shock acted in a fashion similar to glucocorticoids in inhibiting mouse peritoneal macrophages and increased the transfer of glucocorticoid receptors to the nucleus. Snyder et. al (1992) found that mouse peritoneal macrophages synthesized heat-shock proteins (HSPs) maximally after a 12-minute exposure to 45° C.; HSPs were only found two to six hours after heat treatment. They found no HSP-70 at 42° C. or 43° C. At 2 and 24 hours after heating, phagocytosis was normal. They did not mention whether macrophages entered apoptosis with this treatment and that the same treatment (12 minutes at 45° C.) decreased TNF alpha and IL-1 RNA synthesis in mouse peritoneal macrophages. Pizurki et. al (1994) reported that circulating human monocytes express HSPs two hours after 20 minutes of exposure at 45° C. and that HSP expression was enhanced in the presence of cAMP and unaffected by indomethacin.

A number of studies have shown that heating and chemical treatments change the activity of immune cells. Chen (1987) found that heating murine macrophages to 41° C. to 43° C. for one hour caused them to synthesize and release prostaglandins of the E type. Fouqueray (1992) found that a 20-minute exposure of rat peritoneal macrophages to 39° C. to 41° C. decreased synthesis of tumor necrosis factor alpha and interleukin-1 within two hours, but monocytes circulating in the blood were less sensitive to heating than were the tissue macrophages. Ribeiro (1996) confirmed that heat exposure decreases macrophage release of TNF alpha both in vitro and in vivo. Kunkel (1986) showed that indomethacin inhibited lipopolysaccharide (LPS)-induced synthesis of prostaglandins by macrophages (and inhibited heat-induced PGEs (Chen, 1987) but enhanced macrophage production of TNF-I in response to LPS. Morange M. (1986) found that HSPs were induced at lower temperatures when cells were exposed to interferonalpha and interferon-beta. Ensor (1995) reported that exposing a macrophage cell line to 40° C. for 30 minutes prevented (within six hours) synthesis and release of TNF-I in response exposure to LPS. The half-life of TNF-I mRNA was shortened. There was no change in the levels of MRNA for GAPDH, θ-actin or IL-6. HSP-72 was increased at 43° C. The same authors previously showed that in human macrophages TNF expression was suppressed at 38.5° C., but HSP-72 was increased only above 40° C. Papadimitriou showed that macrophage apoptosis was minimal at 39° C. but substantial at 41° C.

Although the cellular phenomenon of apoptosis has been studied in some detail in tissue culture, no studies have been directed toward developing that technique for the treatment of inflammation. New methods are needed for treating inflamed body tissues and in particular to the treatment of atherosclerotic plaques to prevent rupture. Such methods should not induce an inflammatory response and should be capable of eliminating or neutralizing macrophages or other inflammatory cells without damaging blood vessel walls. Novel methods for selectively inducing apoptosis are also needed. Such methods will be useful in preventing the rupture of atherosclerotic plaques and therefore reduce the risk of death from myocardial infarction or stroke.

Stents

An intravascular stent is typically an expandable stainless steel wire mesh cylinder that is transported in compressed form into the lumen of a vessel by means of a catheter. Once the desired site is reached, the stent is deployed so that it presses against the vessel wall to mechanically hold the lumen open. Aside from metals and memory metal alloys, plastics have also been used to form stents. Over the last decade, cardiovascular stent implantation has become a preferred mode of treatment following angioplasty and atherectomy procedures, and is now widely used in interventional centers throughout the United States and other countries. While various stent devices have almost always improved short-term results in vessel patency, at the present time it is not yet determined whether any of the many stent designs and materials have significant advantages over the others. For example, some stents penetrate the plaque, whereby a gruel-like material is extruded through the strut lattice, provoking an intense thrombotic and inflammatory response. Other stent designs merely compress the plaque mass with less disruption of the plaque core. The long-term outcomes with presently available stents, particularly their ability to inhibit restenosis at the site of implantation, are still to be determined. (See Topol et al. 1998; Oesterle et al. 1998). Particular problems that have been associated with stents include thrombus formation and cellular overgrowth. During stent placement the blood vessel wall can be disturbed or injured, and thrombosis often results at the injured site, causing stenosis (narrowing) or complete blockage of the vessel. The basic principle that extensive medial injury leads to more inflammation is common to all coronary interventions. Rupture of a necrotic core, with exposure of the plaque contents, appears to be a potent stimulus for inflammation and profuse proliferation of smooth muscle cells (Oesterle et al., 1998).

Stents that remain in place in a patient for an extended period of time also provide a setting for thrombus formation and for overgrowth of vascular smooth muscle cells on the device itself, which contributes further to stenosis, sometimes referred to as "in-stent restenosis." For example, P. W. Serruys has shown (in the "Handbook of Coronary Stents" Martin Dunitz Ltd., London 1997, in FIG. 1.3 on p. 2) by an electron microscope scan of a wall stent at three days post-implantation that deposits of leukocytes, platelets and thrombus adhere to the wire mesh, and that there is some protrusion of the vessel wall into the lumen. These deposits are thrombotic and mitotic, eventually causing neointimal proliferation and thombotic regions. As a result, the patient is placed at risk of a variety of complications, including heart attack, pulmonary embolism, and stroke, depending on the placement of the stent.

In addition to the plaque extruding tendency of lattice-like stent designs, the metal composition and other characteristics of the stent surface are also believed to be important factors for the performance of an implanted stent. It is well established that stainless steel implants such as pacemakers tend to release chromium and nickel ions, which can destroy or damage certain enzymes and proteins and can exacerbate allergies to these metals.

Non-metallic stents have also been used for endovascular support. These devices are generally cylindrical structures made up of a sheet or sleeve of resilient, elastic material which can be cured or hardened following delivery of the stent to a selected region of a vessel. For example, U.S. Pat. No. 5,100,429 (Sinofsky) discloses an endovascular stent having a tubular body formed as a rolled sheet of a biologically compatible material having a cross-linkable adhesive material between overlapping portions of the rolled sheet. U.S. Pat. No. 5,591,199 (Porter) is for a vascular stent made up of a biocompatible fibrous material that is coated or filled with a curable material so that the fiber composite can be shaped and cured to maintain the shape. U.S. Pat. No. 5,282,848 (Schmitt et al.) discloses a self-supporting stent having a continuous uniform surface made up of a woven synthetic material. U.S. Pat. No. 5,814,063 (Freitag)

describes a method of embedding the supporting metal stent structure in a cylindrical elastomeric casing such as silicone. However, a potential problem with the sleeve or sheet type of stent is that blood may not adequately circulate to the vessel wall adjacent the stent. Fully covering the endothelium of the vessel wall is also undesirable as the endothelium plays an essential role in biologic activity of the coronary artery, such as fibrinolysis and vasodilation.

Application of a biocompatible coating to a metal stent is currently the most widely-used technique for avoiding problems encountered with bare metal stents. For example, the DIAMOND™ stent produced by the Phytis Company of Hamburg, Germany has been shown to avoid these metal diffusion problems. Smooth coatings can significantly reduce the surface roughness of the bare metal surface to improve hydrodynamic behavior and to deter adsorption of proteins, which leads to thrombus formation. The phosphorylcholine-coated stent manufactured by Biocompatibles Ltd., Farnham, Surrey, UK, is an example of a more hemocompatible metal-based stent.

Stent-coating materials that have been used to decrease the inherent thrombogenicity of stents and/or reducing in-stent restenosis include the following synthetic substances: polyurethane, segmented polyurethaneurea/heparin, poly-L-lactic acid, cellulose ester, polyethylene glycol and polyphosphate ester. Thrombus inhibitors and other therapeutic agents have also been incorporated into the fiber matrix of non-metallic stents, or attached to a biocompatible coating that encapsulates a stent. Some of the naturally occurring substances that have been described as biocompatible or therapeutic coatings for stents include: collagen/laminin, heparin, fibrin, phosphorylcholine, AZ1 (monoclonal antibody directed against rabbit platelet integrin $\alpha_{IIb}\beta_3$) absorbed to cellulose, and AZ1/UK (monoclonal antibody directed against rabbit platelet integrin $\alpha_{IIb}\beta_3$/urokinase conjugate) adsorbed to cellulose. (Topol et al., 1998).

U.S. Pat. No. 5,749,915 (Slepian) describes a method of forming a biocompatible polymer coating on a vessel wall by providing a biocompatible polymeric material that is non-fluent at body temperature, yet which becomes fluent at an elevated temperature. The material is heated to render it fluent, contacted with a tissue surface to be "paved", and allowed to cool, thereby providing a non-fluent biocompatible polymeric covering on the vessel wall.

Therapeutic stents have also been described as vehicles for prolonged local drug administration, as means for delivery of gene therapy to cells of the arterial wall, and as carriers of viable endothelial cells to passivate the stent surface (See Topol et al., 1998). U.S. Pat. No. 5,674,192 (Sahatjian, et al.) describes a drug-carrying balloon catheter and stent with a polymer coating such as a swellable hydrogel incorporating the drug. The expandable portion of the catheter can be adapted for application of heat to the polymer material to control the rate of administration. The polymer is meltable and the release of the polymer is aided by the application of heat.

U.S. Pat. No. 5,906,636 (Casscells, et al.) discloses use of an endolumenal stent to gently heat an inflamed atherosclerotic plaque for reducing inflammation and/or inducing apoptosis in plaque cells as a means for preventing or delaying restenosis after angioplasty or stenting.

The use of electromagnetic energy, including microwave, radio frequency (RF), coherent (laser), ultraviolet (UV) and visible-spectrum light energy, have been used in various angioplasty and atherectomy devices, endeavoring to destroy plaque without harming the vessel wall. For example, U.S. Pat. No. 5,057,106 (Kasevich) discloses the use of microwave energy for heating atherosclerotic plaque in the arterial wall in combination with dilation angioplasty. U.S. Pat. No. 4,807,620 (Strul) and U.S. Pat. No. 5,087,256 (Taylor) provide representative examples of atherectomy or angioplasty devices that convert electromagnetic RF energy to thermal energy. U.S. Pat. No. 5,053,033 (Clarke) describes the use of an UV laser to inhibit restenosis by irradiation of smooth muscle cells with non-ablative cytotoxic light energy. U.S. Pat. No. 4,997,431 (Isner); U.S. Pat. No. 5,106,386 (Isner); U.S. Pat. No. 5,026,367 (Leckrone); U.S. Pat. No. 5,109,859 (Jenkins); and U.S. Pat. No. 4,846,171 (Kauphusman) each disclose the use of laser light transmitted via an optical fiber or conduit to reduce tissue mass or remove arterial plaque by ablation. U.S. Pat. No. 4,878,492 (Sinofsky) and U.S. Pat. No. 4,779,479 (Spears) describe the use of nonablative laser light energy of sufficient wattage to heat the arterial plaque during a conventional PTCA dilation procedure in order to fuse fragmented plaque and coagulate trapped blood. Typically, these kinds of devices fail to distinguish normal vessel wall from atherosclerotic plaque, however.

Stent-type devices have also been employed for thermal therapy of various annular organs and vessels, almost all of which are directed at inhibiting or killing cancer cells and typically generate temperatures in the cell necrosing range and beyond. Goldberg (1997) has described one type of heating stent for applying RF energy to indwelling metallic stents to induce transluminal coagulative necrosis. Another type of heating stent is disclosed in Japanese Pat. No. 6063154 (Koji et al.), which describes a heat generating stent for placement in an annular organ for tumor treatment. The hollow stent is made of a thermosensitive magnetic material that is heated by an external high-energy, alternating magnetic field. Similarly, Japanese Pat. No. 6063155 (Koji et al.) describes the application of a thermosensitive medicine-containing polymer to the thermosensitive magnetic stent to provide temperature-controlled treatment of an annular organ or vessel.

However, problems may arise when the body is exposed to a high electromagnetic field. For instance, other implanted metallic objects in the body, such as pacemakers, defibrillators or cardiovascular stents, may malfunction or heat up dangerously if exposed to a strong electromagnetic field. Additionally, the effects of high magnetic fields on biological tissue are still not completely understood. Such fields may cause ionization of some biomolecules and cellular damage. Another disadvantage of techniques requiring high-energy magnetic field production is that they require facilities that are costly to maintain and are not widely available to the medical community.

Other methods of heating vessels or other annular organs, such as resistive heating of a fluid-filled balloon catheter, for example, which require passage of electricity to the body are inherently difficult to control and can also present a hazard to the patient. Moreover, all of the conventional intravascular heating methods are invasive and catheter-based.

Ultrasound (US) is another energy source that is applied to the body and is particularly well known for its diagnostic imaging utility, particularly in monitoring fetal development and for echocardiography in the diagnosis of cardiac conditions. Ultrasound is generally considered to be a safe diagnostic and therapeutic tool when employed clinically, and the beneficial therapeutic effects—both thermal and non-thermal—of ultrasound in physical therapy are widely recognized, particularly for wound healing and in reducing pain. (See, for example, McDiarnid, et al. 1987). Therapeutic use of ultrasound for cardiovascular-related conditions include, for example, enhancement of thrombolysis by transcutaneous ultrasound treatment, as described by Luo et al. (1998). Intravascular ultrasound (IVUS) imaging is currently being used to assist stent implantation (Oesterle, 1998). U.S. Pat. No. 5,836,896 (Rosenschein) describes a method of inhibiting restenosis by applying intravascular ultrasonic energy to smooth muscle cells of the vessel wall in order to inhibit the migration and adherence of smooth muscle cells. This method, however, takes advantage of the non-thermal effect of ultrasound to produce cavitation within a vessel in a region of angioplasty or atherectomy injury.

Diagnostic and therapeutic uses of ultrasound are based on the fact that almost every substance has a characteristic acoustic impedance, which is based on the speed at which ultrasound waves travel in that substance, or medium. Ultrasound waves may move, or propagate, through a medium more or less freely, or they can be absorbed, reflected or scattered by the molecules of the medium. It is the relative contribution of each of these factors that determines the speed at which ultrasound will travel in a given medium. Resistance to movement due to absorbance, reflectance or scattering is generally termed "acoustic impedance." The acoustic impedance of a substance is equal to the product of the density of the substance and the speed of sound therein.

Accordingly, each tissue in the body will absorb a certain percentage of the energy from ultrasound waves that propagate through it. Ultrasound travels at a speed of about $1.5 \times 10^5$ cm/s in most soft tissues. When an ultrasound wave is absorbed, or partly absorbed by tissue, the associated kinetic energy is converted to thermal or heat energy, raising the temperature of the tissue a corresponding amount. At the interface between two acoustically different tissues, such as bone and soft tissue in the body, even more heat is generated by the ultrasound due to reflectance by the denser medium. Reflectance can produce "standing waves," as discussed by Roy Williams (1987). Recent tests of the effects of ultrasound irradiation on non-living porcine tissue, when placed on both metal and plastic surfaces, were performed by Robertson et al. (1995). The results of those studies showed a markedly higher maximum temperature increase in the tissue, and a significantly greater initial rate of heating, when the tissue was on the metal surface rather than on the plastic surface. Ultrasound, particularly pulsed high intensity ultrasound, can quickly cause excessive heating and even burning of soft tissue in contact with bone or another acoustically reflective object, such as a conventional metal stent, unless the conditions are carefully controlled.

Even though ultrasound has been in use both diagnostically and therapeutically for over a decade, and its beneficial results have been attributed to both thermal and non-thermal effects, there has been little research on the effect of treatment dosage on the extent of tissue heating. (See, for example, Kimura et al. 1998). Barnett et al. (1994) have reported that exposure to even diagnostic levels of low intensity ultrasound produce significant temperature increases in vivo, specifically at interfaces between bone and soft tissue. Fan and Hynynen (1992) have reported the effect of wave reflection and refraction at soft tissue interfaces during ultrasound hyperthermia treatments. A temperature increase of more than 5° C. has been reported with diagnostic ultrasound equipment, using either pulsed-wave or continuous-wave low intensity ultrasound for tissue close to bone S. Barnett (1998). Wells (1992)) focuses on the biological effects due to heating by diagnostic ultrasound, with particular reference to the monitoring of prenatal development of animals.

Today, ultrasound thermal therapy is only used for heat delivery to large volumes of tissue, such as tumors, to burn sites of internal bleeding to achieve coagulation and clot formation, and for physical therapy. High intensity focused ultrasound is effective for heating cancerous tissue, typically increasing the temperature of the target tissue by about 10–20° C. and often up to about 85° C. High intensity ultrasound is also used to stop bleeding, in lithotripsy procedures, and for deep surgery. For example, the SONABLATE™ acoustic ablation device (Focus Surgery, Inc., Indianapolis, Ind.) is reported to permit bloodless noninvasive surgery in all parts of the body. Generally, in tissues where heat removal by blood flow or by conduction is significant, higher energy pulsed beams of focused ultrasound are sometimes employed in order to more quickly achieve the desired level of heating at a target site. Thermal therapy devices have particular difficulty in establishing and maintaining the desired therapeutic temperature in highly perfused tissues. Also, blood flowing through an artery makes it very difficult to heat a region of the vessel to a desired temperature. Oftentimes, considerable damage to intervening tissue also occurs as a consequence of the higher energy ultrasound required with existing ultrasound thermal treatment methods.

Conventional metal stents, when exposed to a focused high intensity ultrasound beam may cause damage or burning of the surrounding cardiovascular tissue due to reflectance by the metallic surface of the stent. It would be desirable to have safer stents that could avoid at least some of the problems typically encountered with conventional stents, as described above. A non-invasive way to apply thermal therapy intravascularly would be particularly advantageous over the existing catheter-based techniques. It would be even more desirable to have a way to utilize existing ultrasound technology to achieve controlled heating of stents for particular therapeutic or diagnostic applications, while avoiding inadvertent or excessive heating and damage to intervening or non-targeted body tissue.

SUMMARY OF THE INVENTION

The present invention provides methods that can be used to treat inflammation in body tissues and in particular to treat inflamed atherosclerotic plaques. The methods can be used to decrease or eliminate inflammation in a plaque to prevent rupture. Certain disclosed methods are particularly useful for inducing apoptosis in localized cell clusters such as the macrophages that cause an inflammatory response.

The present methods utilize localized and mild hyperthermic treatments to neutralize or preferably to induce apoptosis in inflammatory cells. Localized heat treatments avoid systemic cell damage and at the same time lead to clearance of unwanted cells without causing a secondary inflammation.

The techniques disclosed herein are useful in the treatment of inflammation. The term inflammation includes inflamed atherosclerotic plaques; restenosis; and arteritis such as that found in systemic lupus, Takayasu's arteritis, Beheet's syndrome, temporal (gran+cell) arteritis, myocarditis of the autoimmune etiology; arteriovenous fistulea, dialysis grafts or other vascular prosthesis. The phrase "treating inflammation" also includes treating a region of a vein prior to or after balloon angioplasty, rotational or directional atherectomy, stenting or related interventions that could result in inflammation and subsequent thrombosis, acute closure or restenosis. Use of the disclosed methods on atherosclerotic plaques will reduce the chance of myocardial infarction or stroke.

Certain methods of the present invention are useful for inducing apoptosis in inflammatory cells. Inflammatory cells primarily consist of macrophages and other closely related cells of the immune system that are involved in creating inflammation. The present methods specifically contemplate inducing apoptosis in these cells with hyperthermic treatments.

Some of the present methods are directed to treating inflamed regions containing deleterious immune cells with heat in the range of 38.5° C.–44° C. for between about 5 minutes to 60 minutes and more typically for at least about 15 to 30 minutes. At the high end of the temperature range, from about 41° C. to 44° C., apoptosis is more effectively induced. Temperatures above 44° C. are not preferred because they begin to cause cell killing through necrosis and pathways that cause secondary inflammation. Treatments at the low end of the temperature range may also be effective. For example, heating with temperatures in the range of 38.5° C. to 40° C., which are below those necessary to cause apoptosis on brief exposures (e.g., 15 minutes) can be used to decrease macrophage production and their release of cytokines. These temperatures are contemplated to be within the present invention. Generally, temperatures of approximately 42° C. to 43° C. will be used.

In patients, following routine angiography, a heat detecting probe, such as is described in U.S. pat. app. Ser. No. 08/717,449, would be used to identify lesions that are significantly hotter than the rest of the artery. Lesions at higher risk of rupture are about two degrees warmer than adjacent tissue. These lesions are detectable by heat imaging catheters consisting of any of several fibers that conduct heat, bundled into a standard coronary or other angiographic catheter ranging from 4 French to 14 French in diameter. Alternatively, a catheter with standard heat sensing electrodes on its surface could be used. In one embodiment, this would be a balloon catheter made of a compliant (soft) balloon material, so as not to damage the endothelium or disrupt the plaque itself.

Heat may be transferred to the target cells by a variety of methods. For example, heat may be transferred into an inflamed plaque in a blood vessel by means of a catheter. Several catheters are commercially available that are capable of introducing the heat required for these techniques. In addition, the catheter disclosed in U.S. patent application Ser. No. 08/717,449 can easily be equipped to emit infrared radiation by one of skill in the catheter arts. Preferred catheters are those that can deliver heat within the temperature range of 38.5–44° C. Catheters that emit heat above about 45° C. are not preferred because the use of such elevated temperatures may damage endothelial cells and produce a secondary inflammatory response.

Preferred embodiments of the present invention introduce heat into a region of inflamed tissue by introducing a stent into the lumen of a blood vessel or the lumen of an organ to treat inflammation in blood vessels, parenchymal smooth muscle cells or interstitial cells such as fibroblasts to prevent obstruction and/or thrombosis in the lumen. Methods for positioning stents are well known in the art. The stent is positioned in such a way as to be in thermal contact with a region of inflamed tissue. The stent is then heated. It can be heated electrically or with microwave or radio frequency radiation or other means. These heating methods can be produced from devices such as catheters within the lumen or from energy sources such as radiofrequency sources outside the body. It would be clear to one of skill in the art that the stent used in such an application must be able to transmit heat. The preferred stents are made of metal.

Although the present techniques primarily rely upon heating methods, chemical agents or radiation may also be employed to augment the effectiveness of heat treatments. For example, beta-blocking drugs, cytokines such as insulin-like growth factor, transforming growth factor B1, vascular endothelial growth factor, fibroblast growth factor, tumor necrosis factor and the like may be used to enhance the susceptibility of macrophages to heat induced apoptosis or to increase the resistance of endothelial cells to apoptosis. Effective amounts of these drugs can easily be determined by one of skill in the art.

Preferred embodiments of the present invention include ultrasonically heatable stents containing biocompatible material that heats more rapidly than does human soft tissue when a focused beam of ultrasound is directed onto the implanted stent. The disclosed methods of the invention provide a new way to invasively or non-invasively heat a tissue which is in contact with one of the coated stents of the invention by directing ultrasound at the implanted stent. The US-heatable stents of the invention also avoid at least some of the problems encountered by other US thermal therapy devices in establishing and maintaining the desired therapeutic temperature in a target tissue, particularly when one is hampered by the presence of blood perfusion in the tissue. Blood flowing through an artery makes it very difficult to heat a region of artery wall to a desired temperature. The ultrasound-absorptive coated stents of the disclosed invention achieve controlled heating for particular therapeutic or diagnostic applications, while avoiding the inadvertent or excessive heating and damage to non-targeted body tissue commonly encountered with other heating stents. The stents of the present invention, and their methods of use, advantageously employ the acoustic impedance properties of tissues and of various biocompatible polymers, among other things. Also, the "double heating" effect that occurs due to reflectance of ultrasound by metal and at dissimilar acoustic interfaces are employed to achieve site-specific therapeutic heating of targeted regions of vessel wall.

As described in more detail below, ultrasonically heatable stents are provided which, after initial endolumenal placement, can be either invasively or non-invasively warmed to produce therapeutic levels of heat in the stent. Similarly, exemplary methods are also described for heating in situ a synthetic vascular graft.

In accordance with the present invention, an ultrasonically heatable stent is provided. The stent may be configured, or designed to maintain the patency of a human vessel, such as a coronary artery, for example. The stent contains an ultrasound-absorptive material that possesses a characteristic acoustic impedance value that is greater than that of living tissue. For the purposes of this disclosure an "ultrasound-absorptive material" is defined as one that absorbs an appreciable amount of the energy of an ultrasound beam whereby the temperature of the material increases. The ultrasound-absorptive material may be used to form the entire structure of the stent. Alternatively, the basic structure or framework of the stent may be made of another material, such as wire mesh, which provides the main support function of the stent and is configured to maintain patency of the vessel. In the latter embodiment, a coating of the ultrasound-absorptive material covers or overlies the stent framework and is characterized by being heatable by ultrasound at a faster rate than living soft tissue. For example, the stent coating may contain at least one US-absorptive material that has a heating rate greater than 0.86° C. per minute when subjected to an ultrasound beam of 1 mHz frequency and 1 Watt/cm$^2$ intensity.

Certain embodiments of the stent include a polymer that has at least one of the US-absorptive coating materials. Examples of some of the synthetic polymers that may be used are silicone, polyvinylchloride, nylon and polyurethane. Combinations of these materials may also be used in order to optimize the heating rate of the coating or to improve stability or biocompatibility of the coating. In some embodiments, the coating also includes a heatreleasable drug for local release at the site of the stent.

In an alternative embodiment of the stent of the present invention, the US-absorptive coat contains at least two layers of US-absorptive material. One of the layers covers at least one other layer, which is sandwiched between the framework and the outer layer. These two or more layers have dissimilar acoustic impedance characteristics. These two layers and their distinct interfaces work together to enhance the ultrasound-induced temperature increase of the coat when exposed to ultrasound. For example, the coating preferably has the characteristic that its temperature will increase 1–5° C. or more in response to ultrasound irradiation at a chosen wave frequency, intensity and duration. The coating will preferably also have the characteristic that its acoustic impedance is greater than that of any intervening tissue located between the stent and an external ultrasound transducer, when said stent is situated in a vessel and ultrasonic radiation is directed toward said stent. This feature prevents tissue in the path of the ultrasonic beam from being damaged or excessively heated before the stent reaches the desired temperature.

Also provided by the present invention is a method of making the new ultrasonically heatable stents. The method includes obtaining a stent framework configured for maintaining patency of a vessel, and obtaining a biocompatible coating material characterized by having an acoustic impedance greater than that of living tissue. The coating material is applied to the stent framework in such a way that the final thickness and character of the coating permits the stent to be heatable by ultrasound at a faster rate than living tissue, as described above.

Also in accordance with the present invention, a method of making an ultrasonically heatable stent is provided. One exemplary stent is made by modifying a basic metal stent framework configured for maintaining patency of a vessel, such as a commercially available wire mesh, or zigzag stent. Over the stent framework is applied a coat or layer of a biocompatible coating material that is characterized by having an acoustic impedance greater than that of living tissue, such as that in the human body. The thickness and other characteristics of the coating are such that said the stent is heatable by ultrasound at a faster rate than living tissue. For example, a heating rate greater than 0.86° C. per minute when subjected to an ultrasound beam of 1 mHz frequency and 1 Watt/cm$^2$ intensity is characteristic of certain coated stents of the invention. One suitable coating material is silicone, and others include nylon, polyvinylchloride, polyurethane and phosphorylcholine, for example. Combinations of coating materials may also be used. The coating may also be applied in layers of the same or different ultrasound-absorptive material, so as to form additional acoustic interfaces. The thickness and manner of coating the stent can be varied such that the resulting coated stent is heatable by ultrasound at a faster rate than the surrounding living tissue. For example, a temperature about 1–5° C. above ambient temperature is generated in the stent.

The present invention also provides a method of treating an atherosclerotic plaque in a living subject. An ultrasonically heatable stent, as described above, is positioned in a vessel lumen in such a way that it contacts a region of vessel wall where an atherosclerotic plaque is located. One particular kind of site in need of treatment is a stenotic plaque that has recently undergone an angioplasty or atherectomy procedure. An ultrasound transducer is advantageously positioned outside of the body of the subject, and operated to cause an ultrasonic beam to be directed onto the stent inside the vessel. For the purposes of this disclosure, the term "advantageously positioned" means that the transducer is located as optimally as possible or practical for directing ultrasound waves toward a particular target. For example, one would try to avoid having hard or interfering surfaces between the transducer and the internal target. Also, positioning the transducer close to the target reduces the depth of penetration of the ultrasound waves required in order to reach the target stent. Due to the choice of ultrasonically heatable coating material covering the stent, and the optimal operation of the ultrasound system, the temperature of the stent is wanned to and maintained at about 1–5° C. above the ambient temperature of the vessel. The ultrasonic heating of the stent is continued while the region of vessel wall contacted by the stent is heated at 38–42° C. for a sufficient period of time to achieve the desired therapeutic goal, such as reducing post-injury inflammation or inhibiting cellular proliferation.

To further optimize the procedure, the temperature of the stent and/or the heated area of vessel wall is measured, using a conventional remote temperature monitoring method. Also, the ultrasound irradiating and temperature measuring steps can be repeated at the desired time intervals, as considered by the user to be medically beneficial. Optionally, but preferably, a microprocessor and visual display system is employed to control the operation of the ultrasound transducer and to receive, analyze and display the temperature measurements. It is also preferred in some embodiments that the ultrasonic transducer operate in the frequency and intensity ranges employed with conventional physical therapy equipment, for example, about 1–3 mHz frequency and 0.8–1.5 Watts/cm$^2$ intensity for a sufficient time to heat and hold the stent at the desired temperature. In some embodiments, at least two transducers are arranged in an array around the body of the patient and each transducer is operated in cooperation with the others so that two or more ultrasonic beams are directed at the stent from different directions. The depth of penetration of the ultrasound signal and the amount of heating obtained with a particular stent is adjusted by tuning the frequency of the ultrasound signals. Also, the width of the beam can be narrowed by conventional means, for example an acoustic lens can be employed to focus on a desired spot, if desired. By choosing a suitable ultrasound heatable material and by advantageously positioning the transducers and adjusting and focusing the ultrasound appropriately, the temperature of the stent is more easily or quickly warmed up to and held in the desired temperature range. For example, the ultrasound heating system is adjusted so that the stent is maintained at about 1–5° C. above ambient vessel temperature for the length of time that is needed to heat the area of vessel wall surrounding the stent at 38–42° C.

In one embodiment of the present invention, a method of treating a site on a vessel wall includes placing an ultrasound transducer inside the esophagus, similar to the transducer placement for conventional trans-esophageal echocardiography. In some embodiments of the method of treating atherosclerotic plaque, an intravascular ultrasound transducer is positioned inside the stent instead of positioning one or more transducers outside the body. This is particularly desirable if another intravascular procedure is being performed on the patient, and the two procedures can be combined.

A method of treating a vascular injury, such as an angioplasty or atherectomy site, for inhibiting restenosis is also provided by the present invention. Similar to the method of treating an atherosclerotic plaque, an ultrasonically heatable stent is positioned along the vessel wall at a site where an angioplasty or atherectomy procedure has been recently performed. The site is subjected first to ultrasound-induced heating at 39–40° C. to reduce post-injury inflammation. This 39–40° C. heating can be repeated in a periodic manner in order to remove any residual or recurring inflammatory deposits on the surface of the stent, as deemed medically necessary. Subsequently, especially if restricted blood flow through said stent is detected, an ultrasound transducer may again be applied such that an ultrasonic beam is directed onto the stent. In the second phase of treatment, the stent is maintained at a temperature about 1–5° C. above ambient vessel temperature long enough to heat any vascular tissue overgrowth and accumulated inflammatory cells to induce apoptosis. For example, the second phase heating could be 42° C. for at least 15 minutes, to induce apoptosis in smooth muscle cells and in macrophages. If desired, the accuracy and ease of performing the procedure can be facilitated by non-invasively monitoring the temperature of the stent or the region of vessel wall. Also, a microprocessor and visual display can be used to receive, analyze and display the temperature measurements.

Another method encompassed by the present invention includes a method of reducing or eliminating a population of inflammatory cells on an implanted synthetic vascular graft, such as an arterio-venous (AV) graft, in a living subject. According to this method, an ultrasound transducer is advantageously positioned with respect to the location of the stent and is operated in such a way that an ultrasonic beam is directed on the graft. In this way the temperature of the graft, or a portion thereof, is increased about 1–5° C. above the ambient vessel temperature. This temperature elevation is maintained for a sufficient period of time to heat the graft, or portion thereof, at a temperature of 38–42° C. As described before, a microprocessor and monitor may be incorporated in the treatment system and ultrasound operation and temperature measurement steps may be repeated at therapeutically beneficial intervals.

Still another embodiment of the present invention provides a method of inhibiting or regressing in-stent restenosis. After an ultrasonically heatable stent of the invention is implanted into the vessel of a subject, vascular and inflammatory cells may invade or over-grow the stent, as sometimes occurs with mesh-type stents. In this case, however, an ultrasound transducer is positioned outside of the body and a low-intensity ultrasonic beam is directed at the stent. The ultrasound beam is operated in such a way that the temperature of the stent is increased to about 1–5° C. above the ambient vessel temperature for a sufficient period of time to heat the stent at a temperature of about 42° C. Optionally, ultrasound irradiation and temperature measurement steps are repeated at therapeutically beneficial time intervals. For example, it is desirable to heat up the stent when blood flow through the stent has become restricted, when overgrowth of vascular smooth muscle cells into the stent is believed to have occurred, or to reduce the size of blood clots in or around the stent. This procedure may also employ a microprocessor and visual display system to control the operation of said ultrasound transducer and to receive, analyze and display said temperature measurements, whereby apoptosis is induced in a population of cells of the overgrown tissue.

DETAILED DESCRIPTION OF PREFERRED EMBODIMENTS

The following examples are offered by way of illustration and are not intended to limit the invention in any manner. All temperatures are in degrees Celsius unless otherwise noted.

Example I

The inventors have discovered that macrophages are more susceptible to heat induced apoptosis than endothelial cells.

This discovery led to the development of the present techniques that use heat to reduce inflammation in inflamed tissue and especially in inflamed atherosclerotic plaques. However, greater sensitivity to heat-induced apoptosis of macrophages is not a requirement of the invention because many athersclerotic plaques are denuded of endothelium in which case induction of endothelial cell apoptosis would be moot.

Figure 1:
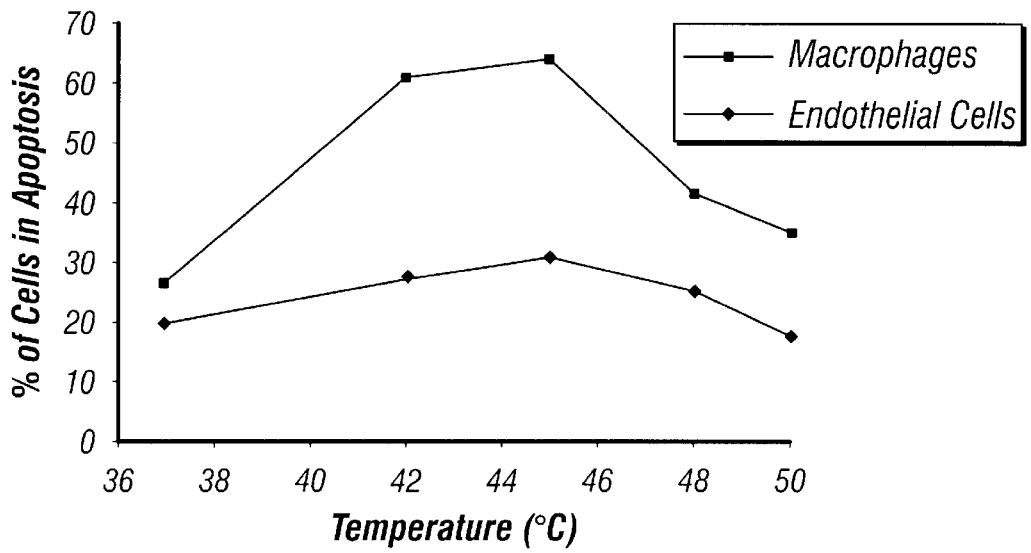
FIG. 1 is a graph showing the percent of cells from Watanabe (atherosclerosis) rabbit aorta tissue undergoing apoptosis after exposure for 15 minutes at the temperatures shown.
Figure 2:
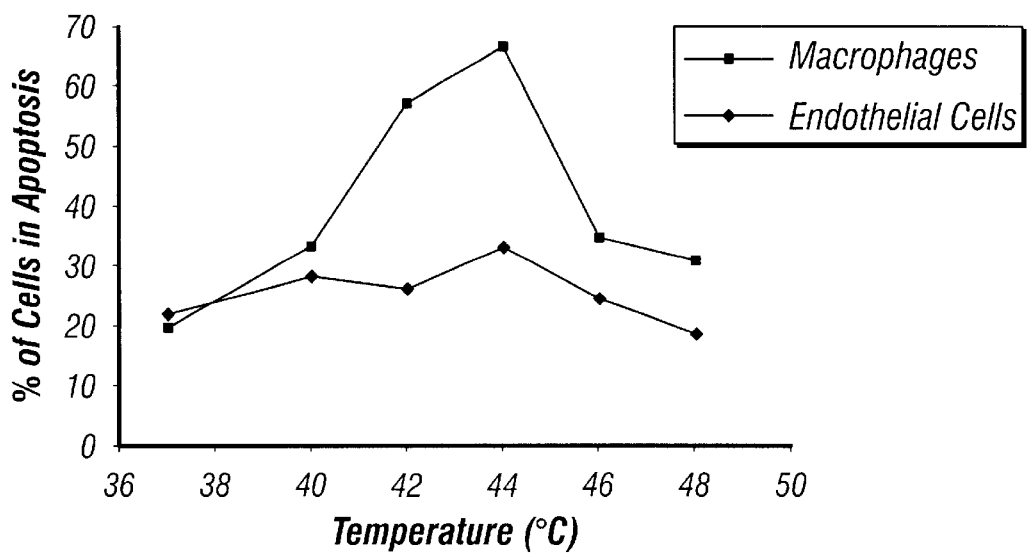
FIG. 2 is a graph showing the percent of cells in apoptosis from human endarterectomy tissue after heating in cell culture for 15 minutes at the temperatures shown.

FIG. 1 shows the percent of cells from Watanabe (atherosclerosis) rabbit aorta tissue undergoing apoptosis after exposure for 15 minutes at the temperatures shown, followed by "TUNEL" staining after a 6 hour incubation at 37° C. FIG. 2 shows similar results when the cells in human carotid artery endarterectomy samples were investigated in a similar manner. Living human carotid atherosclerotic plaque was obtained by endarterectomy, immediately placed in tissue culture and subjected to varying temperatures for fifteen minutes. After four subsequent hours at 37° C. these specimens were fixed and processed for light and electron microscopic histology. The sections were subjected to histochemistry for the enzyme terminal deoxynucelotidyl transferase, which results in a blue color in the apoptotic cell. A kit from Trevigen, Inc (Gaithersburg, Md., 20877) was used with the appropriate positive and negative controls. As a further control the stained cells were evaluated by electron microscopy. The results show a significant number of apoptotic cells at 37° C. There was an increase in the number of apoptotic cells at 42° C. with a peak at 45° C.

These results were confirmed by electron microscopic finding of chromatin margination, protrusions and nuclear fragmentation and budding with the production of membrane bound apoptotic bodies. Light microscopy suggested that almost all of the cells undergoing apoptosis were macrophages. Finally, a minority of endothelial cells underwent apoptosis with 15 minutes of exposure to 45° C., suggesting that there is indeed a window in which the macrophages can selectively be induced to undergo apoptosis.

Figure 3:
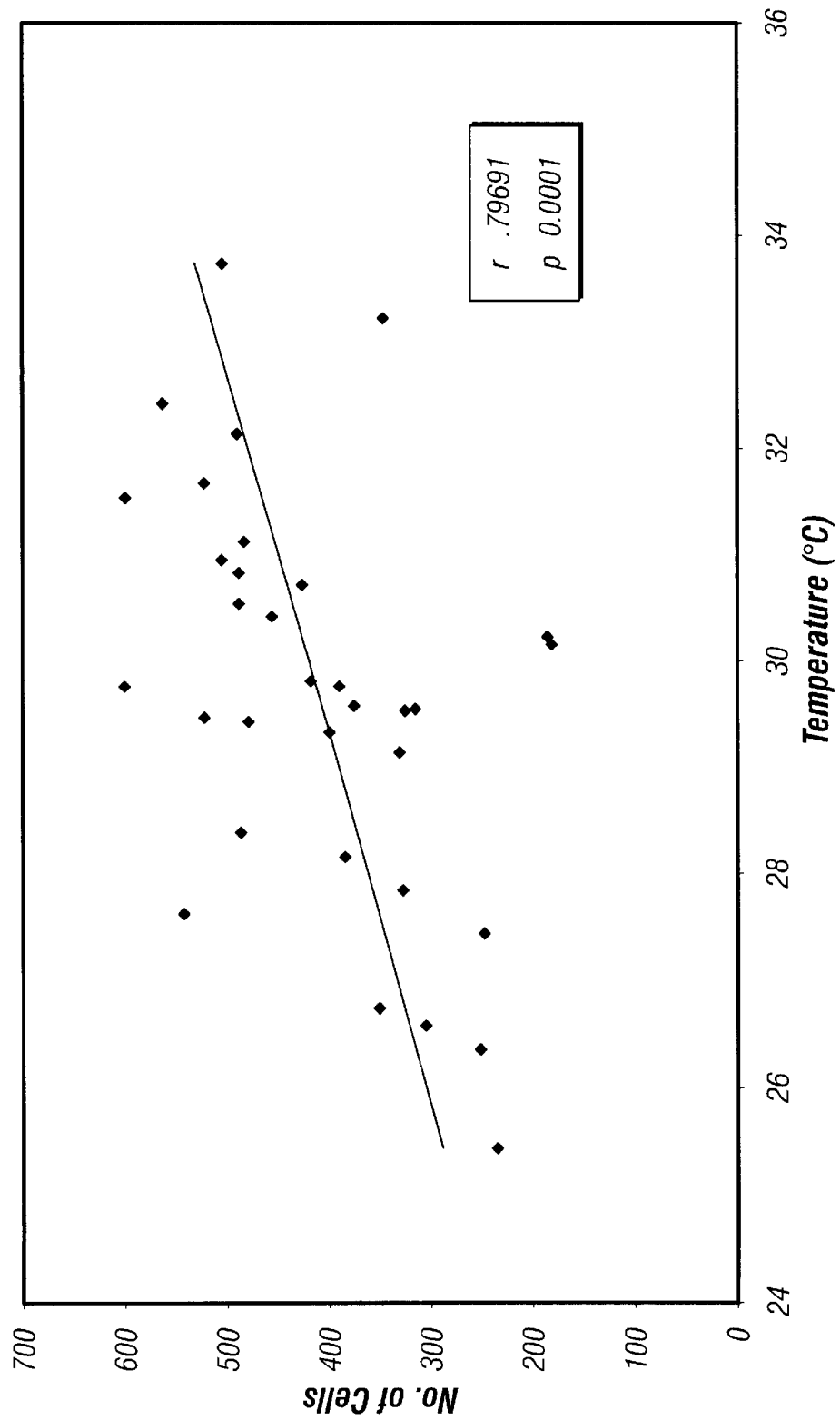
FIG. 3 is a graph showing the relationship of heat as measured by an infrared camera, to cell density in living human carotid endarterectomy specimens.
Figure 4A:
FIG. 4A is a photomicrograph of a representative specimen of human carotid endarterectomy tissue heated to 44° C. for 15 minutes.
Figure 4B:
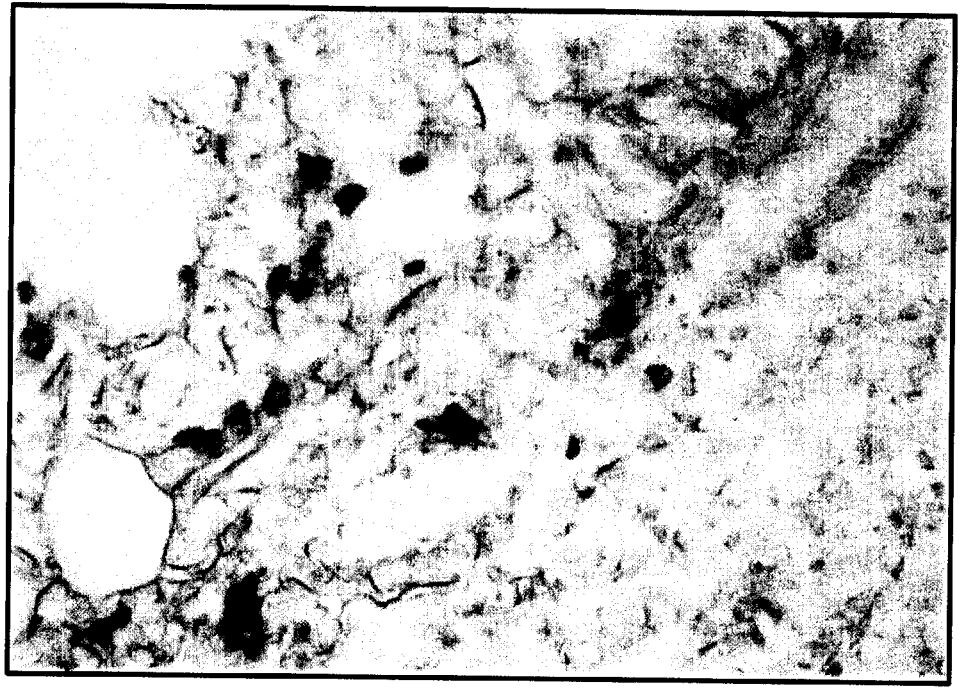
FIG. 4B is a photomicrograph of an unheated portion of the specimen of human carotid endarterectomy tissue shown in FIG. 4A.

FIG. 3 shows more directly the relationship between cell density and heat produced as measured by an infrared camera. The elevated heat produced in areas having elevated numbers of macrophages facilitates a detection method for identifying inflamed plaques as discussed in U.S. patent application Ser. No. 08/717,449. In FIG. 4 is shown the results from a study in which a representative specimen of human carotid endarterectomy tissue was divided and half. One half shown in FIG. 4A was incubated at 44° C. for 15 minutes in a humidified incubator, followed by 6 hours at 37° C. The other half was maintained at body temperature. "TUNEL" staining for DNA was employed to demonstrate apoptosis. The cells are indicated by the dark stain. No counterstain was used in this section. The capillary nuclei are faintly shown as unstained macrophage nuclei. The photograph demonstrates the difference between the nuclei of heated and unheated cells.

Example II

Treatment of Inflamed Plaques

Typically, heat induced apoptosis of inflammatory cells to prevent rupture and/or thrombosis of atherosclerotic plaques in the coronary, carotid, iliac femoral or superficial femoral arteries will be carried out in patients presenting with symptoms of ischemia. For example, patients with angina or a positive stress test, or patients with a recent myocardial infarction who are undergoing coronary angiography, will have an infrared catheter passed down the artery in a fashion similar to that of intravascular ultrasound or angioscopy, as described further below.

Some patients will be referred for this procedure for other reasons. For example, patients having plasma that shows biochemical evidence of inflammation or thrombosis, or endothelial damage or silent myocardial damage, may require coronary catheterization. Alternative tests which might bring non-symptomatic people to coronary angiography and infrared testing might include a magnetic resonance imaging scan which can give a kind of non-invasive thermometry, or positron emission tomography, which gives a non-invasive image of glucose utilization (this may indicate macrophage presence because of their high glucose consumption when activated).

The patients who come for peripheral angiography have come either because of claudication or embolism to the feet or because a doctor has found diminished pulses on physical examination. Patients requiring carotid angiography typically have had a stroke or transient ischemic attack or a bruit has been detected on physical examination or a carotid narrowing has been detected in the course of magnetic resonance imaging, Doppler imaging or angiography performed for other reasons.

In the patients described above, following routine angiography, a heat detecting probe, such as is described in U.S. pat. application Ser. No. 08/717,449, will be used to identify lesions that are significantly hotter than the rest of the artery. Lesions at higher risk of rupture are generally about two degrees warmer than adjacent tissue. These lesions could be detected by an imaging catheter consisting of any of several fibers that conduct heat, bundled into a standard coronary or other angiographic catheter ranging from four French to seven French in diameter. Alternatively, a catheter with standard electrodes on its surface could be used. In one method this will be a balloon catheter made of a compliant (soft) balloon material, so as not to damage the endothelium or disrupt the plaque itself.

Additional evidence that a particular lesion may pose a high risk to the patient, even though the stenosis may be no more than twenty or thirty percent in cross sectional diameter, may be provided by other techniques such as intravascular ultrasound (to determine how thin the fibrous cap is), optical coherence tomography which detects cracks in the plaque surface, and/or angioscopy which detects superficial thrombosis.

Treatment of an inflamed lesion will be performed in several ways. One method is to gently heat the inflamed tissue with heat from about 38.5° C. to approximately 44° C. The treatment is gentle so as not cause cell death due to protein denaturation, desiccation, vesication and/or necrosis. This heating step will be carried out for approximately 15 minutes. This treatment will trigger programmed cell death (apoptosis) in the inflammatory cells and spares endothelial cells. A catheter equipped to radiate heat will be used in this method by placing the tip at the location of the "hot" plaque and directing heat into the plaque. Subsequently, thermography can be repeated to determine the success of the treatment.

Lower amounts of heat will also be used to treat inflamed tissue. For example, heating to 38.5° to 41° (which induces apoptosis in a smaller percentage of macrophages) will have the beneficial effect of decreasing inflammation produced by macrophages by reducing the production of cytokines such as interleukin 1 and interferon gamma. Likewise heating times can be varied. Thus, it is envisioned that some treatments will be for approximately 60 minutes, particularly when lower temperatures will be used. In some cases heating times may be as short as 5 minutes, especially when higher temperatures will be used.

Adjunctive treatments will include the use of cytokines that are known to deactivate macrophages. Examples of cytokines envisioned for these treatments include TGF-B1 and TNF-I. Other adjunctive therapies will be those directed to preventing the attachment of cytokines to their receptors, the attachment of monocytes, lymphocytes or neutrophils to cells, the expression of selectins or cytokines or chemotactic factors by endothelial cells, soluble receptors and other antagonists of inflammatory cytokines and chemotactic factors, as well as chemical treatments that destroy inflammatory cells.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, a catheter equipped with a laser or other heat source can be substituted for a catheter that produces infrared radiation. In addition, this technique could be adapted to prevent or delay the onset of tissue rejection and treatments of other inflamed tissues, such as restenosis after balloon angioplasty or related interventions including stenting and rotational or directional atherectomy (since macrophage density in these tissues predicts restenosis (Moreno) elimination of macrophages by heat-induction of apoptosis will reduce the likelihood that restenosis will occur). Another application will be stenosis of arteriovenous fistulae, dialysis grafts, and other vascular prostheses. In these applications, heat therapy can be applied either from within the vessel or across the skin by means of infrared radiation, radiofrequency, heated metal, etc. Still another application would be the use of microwave or radiofrequency to preferentially heat a metal stent to induce macrophage apoptosis to prevent stenosis or resterosis. All such modifications are intended to be included within the scope of the appended claims.

The methods and devices of the present invention take advantage of the properties of certain types of plastics, polymers and other coating materials that make some of them more susceptible to heating than others. For example, some plastics melt when heated to a given temperature, and others do not. The inventors observed that not only do a variety of biocompatible plastics and other conventional coating materials for medical devices differ in their melting temperatures, they also differ in the amount of heating they undergo in response to ultrasound radiation. In the case of ultrasound, the amount of heating that occurs depends upon how large a part of the ultrasound wave is absorbed by a medium and converted to thermal energy. The present invention also takes advantage of the "double heating" effect that occurs with ultrasound irradiation due to reflectance of sound waves at dissimilar acoustical interfaces. "Double heating" means that not only is a medium heated by absorbance of a portion of the primary ultrasound waves, but it is also heated by absorbance of secondary waves that initially propagated through the medium and are reflected back into the medium. This reflectance occurs at the interface between the medium and another medium that has a higher acoustic impedance. As discussed in more detail below, by directing one or more beams of ultrasound from a transducer positioned outside the body onto a plastic-covered stent, for example, the temperature of the vessel tissue surrounding the stent can be increased by about 1–5° C., or more. High reflectance of the metallic stent framework and high US absorbency and good thermal conduction properties of the coating material all contribute to achieving good heating of the surrounding tissue for therapeutic purposes.

Making an Ultrasonically Heatable Therapeutic Stent

A vascular stent such as the commercially available PALMAZ-SCHATZ™ stent (Cordis Corporation (a Johnson & Johnson company), Miami Lakes, Fla.) provides the basic stent structure or framework for the new ultrasonically heatable stent. However, substantially any conventional cardiovascular wire stent that is configured for placement in a vessel of the body would also serve satisfactorily, depending primarily on the user's choice of stent configuration and chemical composition for particular medical applications.

A uniform coating of silicone is then applied to the entire stent base by dipping it into melted or liquified silicone, or an organic solution thereof, and then hardening or drying the silicone to form a smooth coating. Silicone is a preferred coating material, in part, due to its high acoustic impedence and US heating rate relative to that of vessel tissue, and due to its excellent biocompatibility and chemical stability, even under conventional sterilization temperatures. Other desirable polymers that provide good ultrasonically heatable coatings are polyvinylchloride, nylon and polyurethane, and the like. The best coating materials are those that are not only good absorbers of ultrasound, but also receive the ultrasound waves reflected by the metal surface of the stent framework without breaking down. Ideally this "double heating" effect enhances the ability of the coated stent to heat the adjacent tissue in a controlled manner.

Figure 5:
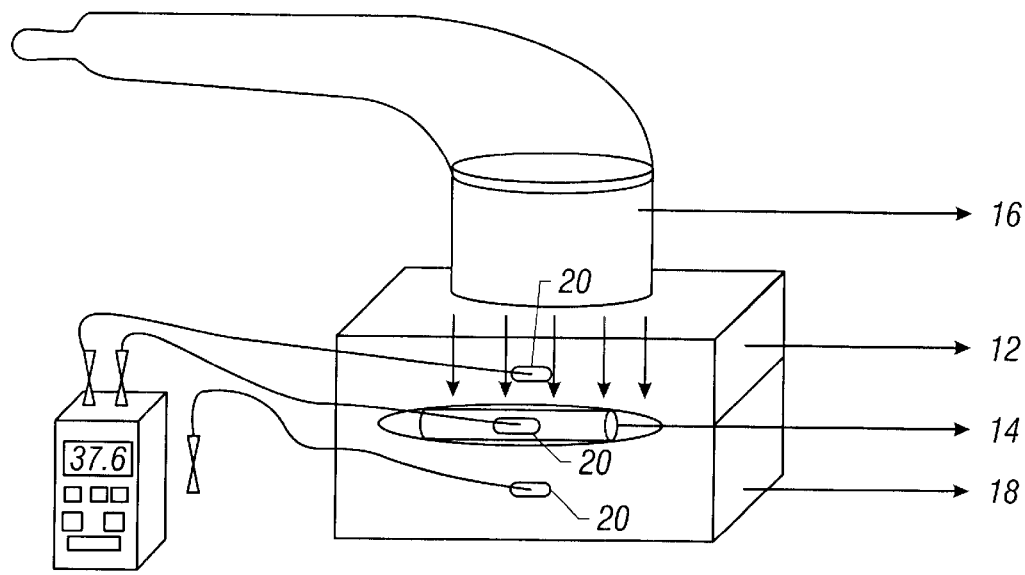
FIG. 5 is a schematic representation of the test set-up for determining the ultrasound heating characteristics of a variety of stent materials.
Figure 6:
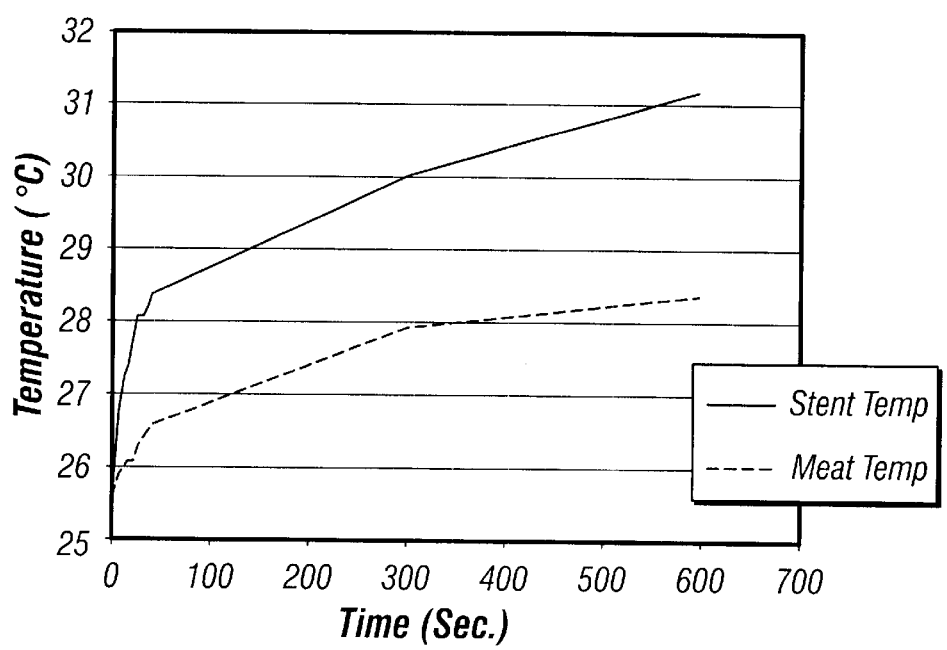
FIG. 6 is a graph showing the ultrasound heating effects (° C./second) of a sample of silicone polymer and a soft-tissue specimen situated between the polymer and an ultrasound transducer operated in continuous-wave mode at an intensity (power) of 1 Watts/cm$^2$.
Figure 7:
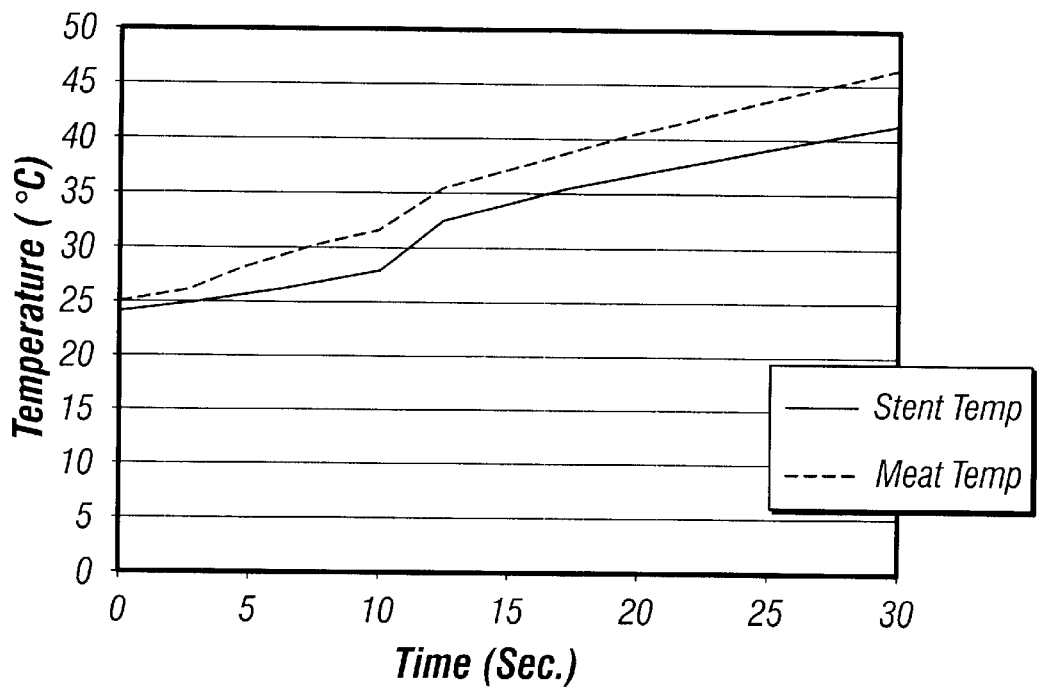
FIG. 7 is a graph showing the ultrasound heating effects (° C./second) of a sample of TEFLON™ polymer and a soft-tissue specimen situated between the polymer and an ultrasound transducer operated in continuous-wave mode at an intensity (power) of 20 Watts/cm$^2$.
Figure 8:
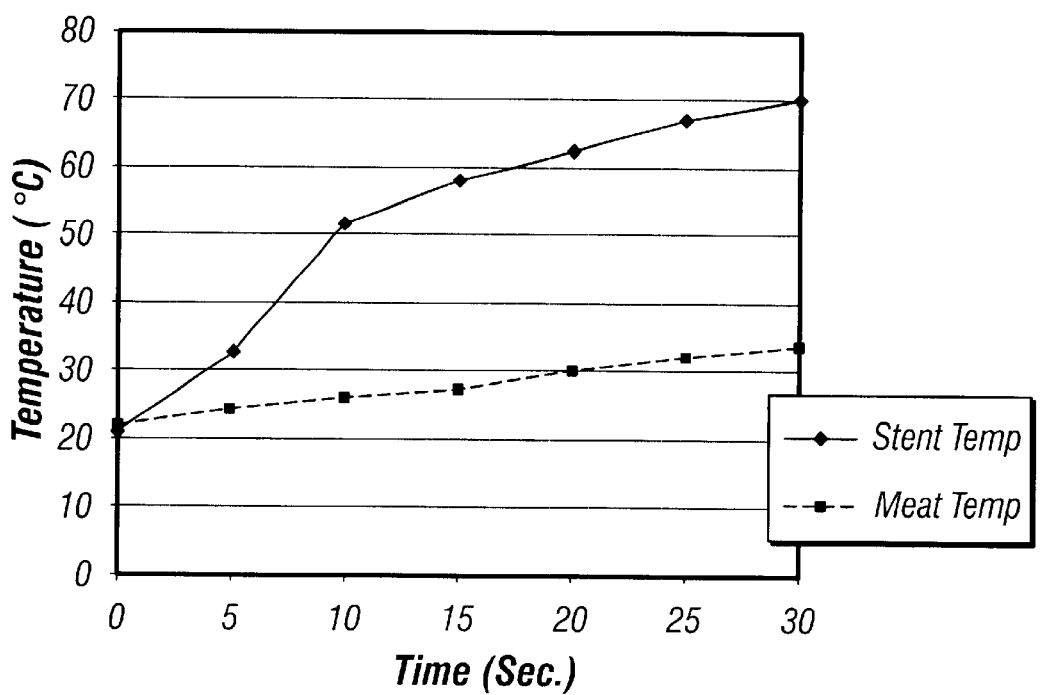
FIG. 8 is a graph showing the ultrasound heating effects (° C./second) of a sample of HAEMOFLO™ polyvinylchloride polymer and a soft-tissue specimen situated between the polymer and an ultrasound transducer operated in continuous-wave mode at an intensity (power) of 20 Watts/cm$^2$.
Figure 9:
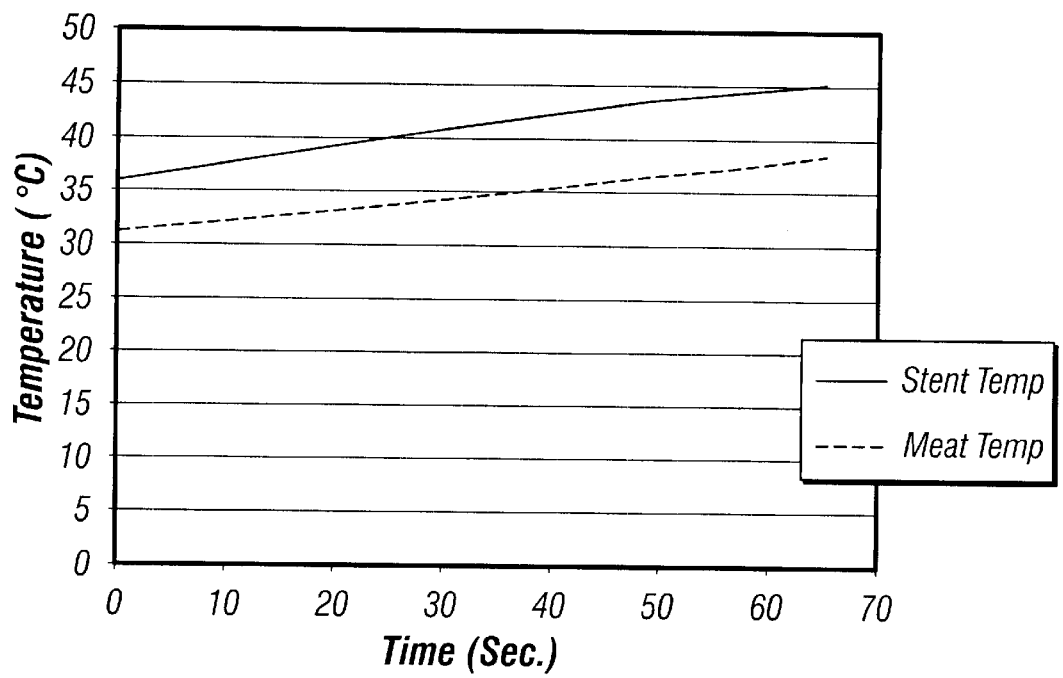
FIG. 9 is a graph showing the ultrasound heating effects (° C./second) of a sample of NYLON™ polymer and a soft-tissue specimen situated between the polymer and an ultrasound transducer operated in continuous-wave mode at an intensity (power) of 5 Watts/cm$^2$.
Figure 10:
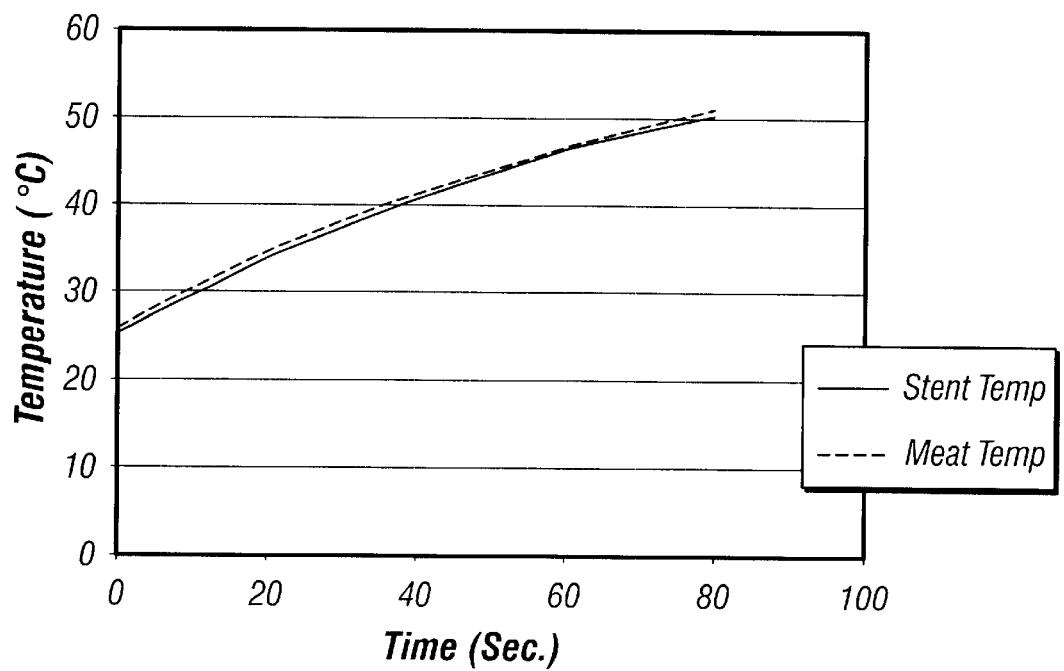
FIG. 10 is a graph showing the ultrasound heating effects (° C./second) of a sample of LEXAN™ polymer and a soft-tissue specimen situated between the polymer and an ultrasound transducer operated in continuous-wave mode at an intensity (power) of 5 Watts/cm$^2$.

Several synthetic polymers were tested in vitro to determine their ultrasound heating characteristics compared to a non-living tissue specimen. A schematic representation of the test set-up is shown in FIG. 5. A first piece of fresh beef muscle tissue 12, representative of human soft tissue, was placed between a sample of polymer material 14 and the ultrasound transducer 16. A second piece of fresh beef muscle tissue 18 was placed below the polymer material 14. The tissue specimens were held at about 4° C. until commencement of the test, whereupon they were equilibrated at room temperature. The temperature of tissues 12 and 18 and of polymer sample 14 at fixed distances from transducer 16 was monitored by way of thermocouples 20, placed as shown in FIG. 5. The ultrasound transducer was operated in continuous-wave mode at an intensity (power) in the range of 1–20 Watts/cm$^2$ and at a frequency of 1 mHz. The heating rates of the various materials are shown in FIGS. 6–11. FIG. 6 is a graph showing the ultrasound heating effects (° C./second) of a sample of silicone and a soft-tissue specimen situated between the polymer and the ultrasound transducer. FIGS. 7–10 are similar graphs for TEFLON™, polyvinylchloride (HAEMOFLO™), NYLON™ and LEXAN™, respectively. These data show that LEXAN™ heated at about the same rate as the intervening tissue, while the intervening tissue heated significantly faster when the "stent" material was TEFLON™. By contrast, silicone and polyvinylchloride samples heated much faster than the tissue. Even nylon was heated by ultrasound at a faster rate than the intervening tissue specimen.

Figure 11:
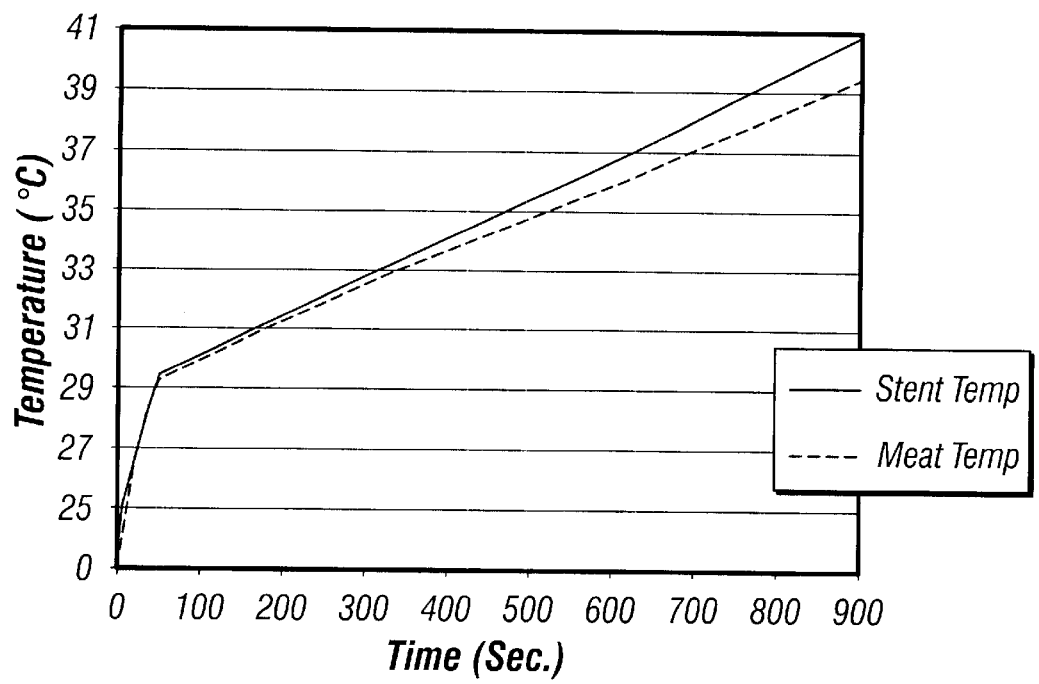
FIG. 11 is a graph showing the ultrasound heating effects (° C./second) due to ultrasound waves reflected from a metal coil stent on a soft-tissue specimen situated between the metal stent and an ultrasound transducer operated in continuous-wave mode at an intensity (power) of 5 Watts/cm$^2$.

The enhanced or double heating effect of ultrasound heating on soft tissue due to reflectance of ultrasound waves back into the tissue can be seen from the graph shown in FIG. 11. A metal coil was placed inside a soft-tissue specimen, similar to the polymer test conditions shown in FIG. 5, with thermocouples located next to the metal coil and inside the tissue. The ultrasound transducer was operated in continuous-wave mode at an intensity (power) of 5 Watts/cm$^2$. It can be readily seen that the temperature of the tissue between the ultrasound transducer and the metal coil increases at about the same rate as the metal coil, at least up to about 300 seconds of continuous ultrasonication at 5 Watts/cm². Given that about 90% of an ultrasound wave is reflected by a metal surface, the temperature of the metal coil in this test should be indicative of the temperature of the adjacent tissue. Comparing the heating rate of tissue using a metal "stent" to the rate using a silicone "stent," it can also be seen that after about 300 seconds the mass of intervening tissue between the metal coil and the transducer was about 3° C. hotter than that between the silicone sample and the transducer. This strongly suggests that a silicone coated stent, for example, can be selectively warmed by ultrasound without excessively warming a mass of intervening tissue, and that the heated stent can warm a small region of immediately adjacent tissue by thermal conduction.

For a given coating material, the thicker the coat, the more heat can be generated by ultrasound irradiation. However, due to differences in acoustic impedance properties of different coating materials, a thinner coat of one polymer may be more desirable than a thicker coat of another polymer, for example. In any case, the polymer coat should not be so thick as to close up the mesh of a wire mesh framework and should not increase the diameter of the finished stent so much that it cannot be readily maneuvered into place in a vessel. The particular coating material that is selected, and the thickness and layering characteristics of the coat, will provide an ultrasound-induced temperature increase of about 1–5° C. when irradiated with low, mid or high intensity ultrasound. The most preferred coating materials are those which permit heating of the stent by low intensity ultrasound. Such coated stents will permit adjacent tissue to be heated at about 38–42° C., by thermal conductance from the coating material. By optimizing the choice of coating material and the reflective interface characteristics, and by fine tuning the depth of penetration and the intensity of the ultrasound beam, the temperature of the stent can be raised a few degrees higher than 5° C., if desired.

As an alternative to using silicone, another biocompatible, chemically stable coating material may be used, provided that it has an acoustic impedance value that is higher than that of the target vessel tissue at the site of placement of the stent. It is essential that the coating material chosen be able to be heated by ultrasound and to conduct heat to the surrounding tissue at a heating rate that is significantly greater than the rate at which the tissue is directly heated by the ultrasound traveling through it. Coatings of choice will not have the acoustic behavior characteristics of metal (i.e., maximum reflectance and minimum absorbency). Other suitable synthetic polymers that may be used for the ultrasonically heatable coating include polyurethane, polyvinylchloride and nylon, for example. An alternative to applying the coating by dipping or spraying, the polymer coating may also be applied by vapor deposition, if appropriate. Examples of polymers that are particularly suited to vapor or plasma deposition onto a metal framework are polyimide, parylene and parylene derivatives. If desired, a mixture of polymers, co-polymers, or other coating materials may be used to optimize the impedance characteristics of the coat. Whichever coating material is selected, it should adhere well to the metal stent structure or framework, should be sterilizable, and should not appreciably detract from the flexibility, strength and other critical features of the basic stent structure. Suitable coatings are at least somewhat elastic and flexible enough to expand and contract along with the underlying stent framework without cracking or splitting, and stable at temperatures up to about 42° C.

If desired, the coating may also include a drug for release at the stent implantation site. In this case, the coating material selected is a US-heatable polymer that releases a portion of the drug upon being heated to a threshold temperature. Of the various naturally occurring substances that have been mentioned as coatings for medical devices, including collagen/laminin, heparin, fibrin, AZ1 (monoclonal antibody directed against rabbit platelet integrin) $\alpha_{IIb}\beta_3$) absorbed to cellulose, and AZ1/UK (monoclonal antibody directed against rabbit platelet integrin aIIbP3/urokinase conjugate) adsorbed to cellulose, some may also be of use in making an ultrasound heatable stent, particularly in combination with a more ultrasound-absorptive material. Inclusion of these types of coating materials may be useful in applications where particular vascular therapeutic effects are desired. An alternative temperature sensitive drug-releasing stent comprises a biodegradable stent material which, after several gentle heating repetitions, becomes completely absorbed or dissolved in the tissue, for example, after about 6 months to a year. Such a stent would provide temperature controlled stent degradation along with timed drug release.

To take further advantage of ultrasound wave reflectance that occurs at interfaces, for the purpose of enhancing the heating properties of the stent, some coating materials may be advantageously applied in discontinuous layers. One way this can be accomplished is by applying multiple thin layers of the same coating material. If desired, one or more different layers of coating material may be applied over the initial coat. This is especially advantageous if additional "double heating" effects are needed to produce a higher temperature in the coating of the therapeutic stent, for example, more than about 1–5° C. above ambient. By choosing a first coating material (inner layer) having a higher acoustic impedance than the second (outer) coating, a certain amount of reflectance at the interface of the two dissimilar coating materials can be expected. This is in addition to the reflectance that occurs at the metal/first coating interface and that increases the heating of the inner layer. Another advantage of applying an outer layer is that it could also serve to insulate the body from a less well-tolerated polymer used for the inner coating. For example, a hemocompatible and phosphorylcholine outer coating may be applied over a rapidly heating polymer to provide the advantage of hemocompatability or resistance to clot formation.

Since the tissue around the new stent is warmed primarily by conduction of heat away from the coated stent, the choice of material used for each layer should also take into consideration the relative thermal conductance properties of a material. For many applications it is desirable to limit the thermal conduction through the metal framework and into the circulating blood. Therefore, a coating material with lower thermal conductive properties is preferred on the inside (lumen) of the stent. Since there are suitable materials that absorb more US energy and others that absorb less, a multi-layer coating can be constructed which permits heating of the outside of the stent while isolating the heat from the interior of the stent to prevent overheating of the blood. For some uses, however, such as when in-stent stenosis occurs, it is desirable to heat both sides of the stent. As discussed in more detail below, when the stent is covered with proliferated smooth muscle cells and infiltrated inflammatory cells it is necessary to heat the internal part of the stent in particular.

As an alternative to applying one or more ultrasonically heatable coatings to a metal framework, a satisfactory ultrasonically heatable stent can also be made by forming the entire device, including the framework, out of a suitable biocompatible material. Suitable materials are those that have an acoustic impedance that is greater than that of the vessel tissue. For example, a stent may be molded of a polymer such as silicone. Another biocompatible polymer with suitable acoustic impedence characteristics could also be employed, provided that the stent structure is of sufficient strength to hold open a section of vessel wall. In order to deter conduction of heat from the ultrasonically heatable stent material to the blood passing through the interior of the stent, an insulative coating may be applied to the interior surfaces.

Use of the Ultrasonically Heatable Stent to Heat a Site on a Vessel Wall

In the absence of heat dissipation by blood flow or conduction, most soft tissues in the body experience an increase in temperature at a rate of about 0.86° C. per minute when subjected to an ultrasound beam of 1 mHz at an intensity of 1 Watt/cm$^2$ (R. Williams in "Production and Transmission of Ultrasound," *Physiotherapy*, pp. 5–7 (March/April 1987)). Generally, if higher ultrasonic frequency is applied, the temperature of the tissue will rise at a much faster rate. Also, if a bony or other reflective interface is present to reflect the ultrasound waves back into the nearby tissue, extremely rapid heating of the tissue can result. The depth of penetration of the ultrasound signal and the amount of heating obtained with a particular stent of the present invention is adjusted primarily by tuning the frequency of the ultrasound signals and by choice of placement of the transducers.

A highly preferred use of an ultrasonically heatable endoarterial stent, as exemplified above, is for implantation into a vessel and heat treatment of an angioplasty or atherectomy site. The new stent may be used for the heat treatment of a site of vessel wall injury to reduce the likelihood that restenosis will occur, similar to the methods described in U.S. Pat. No. 5,906,636 (Casscells et al.), the disclosure of which is incorporated herein by reference. The stent is deployed in accordance with established clinical procedures for endolumenal stent placement to achieve vascular patency, for example, in combination with or after balloon angioplasty. Following placement of the stent, ultrasound is focused on the stent from one or more ultrasound transducers that are positioned outside of the body and are situated advantageously for optimizing the ultrasound signal. Alternatively, three-dimensional ultrasound may be used to focus ultrasound beams circumferentially about the stent, to optimize and more uniformly warm a cylindrical section of vessel wall surrounding the stent. In either case, the surrounding vascular tissue is warmed at 38–42° C. for a period of time ranging from 5–50 minutes, depending on the particular short-term or long-term therapeutic goal. For example, for the purpose of reducing post-injury inflammation, such as after balloon angioplasty, it is preferred to initially treat the injured tissue at 39–41° C., whereby it shuts down macrophage production of cytokines, among other inflammation-reducing effects.

Figure 12:
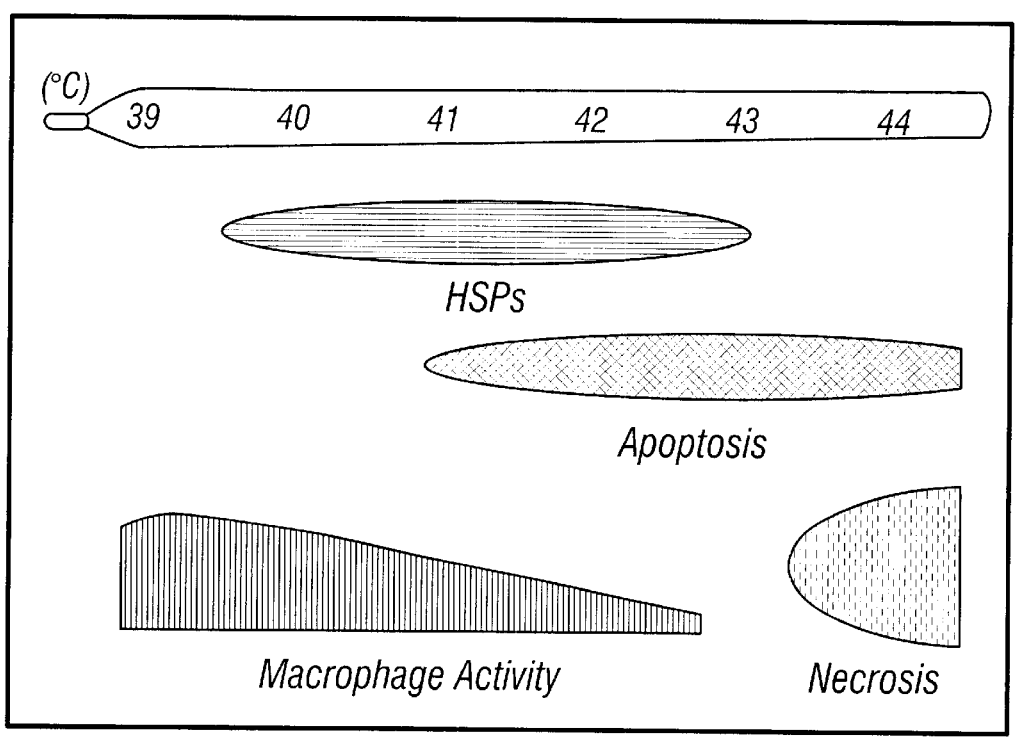
FIG. 12 is a graph showing the predicted effects of heat on macrophages in atherosclerotic plaques.

FIG. 12 shows the temperature ranges over which several reversible and irreversible effects on macrophages in atherosclerotic plaques are expressed. These anti-inflammatory effects include expression of heat shock proteins (HSPs), apoptosis, cellular activity and necrosis. Each of these macrophage effects is represented in FIG. 12 as an elliptical or tapered shape so as to show the range and approximate peak of activity over the approximately 38–44.5° C. temperature range. The inventors have observed that increasing temperature up to 40–41° C. reversibly shuts down macrophage activity, primarily due to expression of heat shock proteins. Beyond that temperature range, apoptosis predominates, peaking near 43° C. At temperatures above about 43° C. the macrophages proceed to necrosis, which is an irreversible outcome. Overall, macrophage activity decreases after 39–40° C. These data strongly suggest that inflammatory cells, particularly macrophages, have a unique "thermostat" or temperature-induced response mechanism which is different from the typical temperature-induced responses of other kinds of cells. It is via this "different" mechanism that the body employs negative feedback to limit inflammation and injury to adjacent cells by inducing excess oxidation and fever. This proposition goes against the generally held view that inflammatory cells necessarily have a very high heat threshold, since they need to function in high stress situations like elevated temperature (fever) and in defensive mode against infectious agents, for example. The inventors' studies also strongly suggest that various stress effects, including increased oxidative stress, appear to be additive in the response of macrophages of atherosclerotic plaque and account for the greater sensitivity of macrophages to gentle heat than other cells. Therefore, by heating a vessel site up to 42° C., deactivation of macrophages occurs and vulnerable plaque can be made more stable. The same concept is true for neointimal formation and smooth muscle cell proliferation in restenotic lesions that are inflammation driven, with macrophage infiltration playing a role.

In certain applications it is desirable to induce apoptosis in cells other than macrophages. In the case of inducing cellular apoptosis primarily in smooth muscle cells of an in-stent lesion, for instance, it is preferred to warm the stent at 42–43° C. for at least 15 minutes. Heating at 42° C. for 15–30 minutes inhibits the proliferation and regrowth of smooth muscle cells and also regresses or reduces the amount of cells and tissue for an extended period of time. This is accomplished without inducing necrosis and the consequential inflammatory response to necrotic bodies, and without incurring injury resulting from release of lysozomal enzymes. Lysozomal enzymes digest extracellular matrix and cause further injury. Use of an ultrasound heated stent to achieve the above-described heating protocols offers a different approach to those of conventional methods of heating atherosclerotic lesions for the purpose of killing cells or fusing proteins.

Since preconditioning of cells through pre-heating (even at sub-apoptotic temperatures) can protect or "innoculate" the cells against apoptosis, it is best to refrain from applying apoptotic thermal treatment until at least 48–72 hours after a prior heat treatment. This is true for inducing apoptosis in macrophages or in other cell types.

During heating cycles, the wave frequency, intensity and duration of the ultrasound are adjusted by the operator, based on preestablished calibration data for the ultrasound system, on the acoustic impedance characteristics of the particular coat composition selected, and, optionally, on temperature measurements, if available. In this way, heating of the stent is optimized and unwanted heating of the intervening tissue is minimized, preventing tissue in the path of the ultrasonic beam from being damaged or excessively heated before the stent reaches the desired temperature. Once a desired temperature is reached in the stent coating using continuous wave ultrasound, the user can change to pulsed US to maintain that temperature. Alternatively, the applied power can be adjusted to regulate the temperature. Low intensity ultrasound is preferred, in a range near to that employed in diagnostic ultrasound procedures, so that the methods described herein can be more widely implemented due to the ready availability of diagnostic range ultrasound equipment. The intensity of the ultrasound should not be exactly the same as the intensity used for conventional echocardiography, however. This prevents any spurious heating of the ultrasound heatable stent that might occur during relatively short term echocardiography procedures. Undesirable heating during routine echocardiography is even less likely due to the fact that no focusing of the ultrasound beam is customarily employed in echocardiography, and the relatively wide beam has little impact on the ultrasound heatable stents of the invention. Although low intensity ultrasound is preferred, if more than about 15 minutes heating time is required to sufficiently warm a stent (for example, to reach 42° C.), the power may be adjusted to mid or high intensity range. If the depth of penetration of the ultrasound signal and the amount of reflective heating can be adequately regulated, the ultrasound heatable coating may be omitted. Under well-controlled conditions, the tissue adjacent the US-reflective metal stent can be carefully heated using reflected US, although this method is less preferred than methods employing the US heatable coated stents because of the difficulty in controlling the extent of heating. In order to get the best vessel wall heating characteristics, it is best to construct the stent in such a way as to provide optimal reflection.

Temperature Measurement by Remote Ultrasound

As discussed above, the acoustic impedance of a given medium is equal to the product of the density of that medium and the speed of sound therein. The speed at which ultrasound travels through a medium also varies with the temperature of the medium. It is this characteristic that makes it possible to remotely measure the temperature of a medium using ultrasound.

In living human tissue the speed of sound increases by approximately 0.08% per degree centigrade and the density decreases by approximately 0.04% per degree centigrade over the applicable temperature range of about 35–50° C. This results in a change of the acoustic impedance of about 0.04% per degree centigrade. It is therefore possible to measure temperature of a locus based on the acoustic impedance of the tissue undergoing examination.

Methods for the non-invasive, non-destructive measurement of the acoustic impedance present in the inside of a subject are well known in the art of medical ultrasound technology. For example, U.S. Pat. No. 5,370,121 (issued to Reichenberger, et al.) describes a method of using ultrasound to measure temperature changes over time in a tissue, such as a tumor undergoing hyperthermic treatment to cause necrosis of the heated tissue. U.S. Pat. No. 4,513,749 (Kino, et. al.) describes a three-dimensional temperature probe for measuring temperature within a localized region of the body. Maass-Moreno et al. (*J Acoust Soc Am* 100:2514–21 (1996) describe another noninvasive method of estimating temperature in tissue based on ultrasound echo-shifts. Accordingly, the temperature of the stent or the adjacent tissue is monitored by one of these established non-invasive techniques.

The particular temperature or heating range chosen should be sufficient to reduce inflammation or to induce apoptosis in inflammatory cells of an existing inflamed atherosclerotic plaque, without causing necrosis in the tissue, following a rationale substantially as taught by Casscells et al. in U.S. Pat. No. 5,906,636 and illustrated in FIG. 12. A preferred treatment regimen includes initially placing the coated stent over a recent angioplasty site. After externally positioning one or more ultrasound transducers, the temperature of the coated stent is gradually raised via ultrasound waves to about 38–41° C. This temperature range is maintained for a sufficient time to produce temporary intracellular anti-inflammatory effects within the macrophage cells at the site, release of inflammatory signaling factors (cytokines) and/or anti-proliferative effects within the smooth muscle cells at the site. Such treatment is aimed at reducing or eliminating residual inflammation from the treatment site. Subsequently, and particularly when reduced blood flow through the stent is detected, the temperature of the coated stent is raised via ultrasound to about 42–42° C., preferably 42° C. for at least 15 minutes. This higher temperature treatment is maintained for a sufficient time to produce permanent anti-inflammatory and/or anti-proliferative cellular effects, including apoptosis. Further heat treatments at similar temperature and duration ranges are optionally applied later, as deemed medically necessary, to deter recurrence of inflammation at the site and/or to inhibit or reduce in-stent restenosis.

In order to avoid possible reflection of ultrasound by hard tissue (bone), the ultrasound waves can be introduced by trans-esophageal approach in which a transducer is located inside the esophagus, similar to the trans-esophageal echocardiography (TEE) procedure. The transducer can thusly be positioned very close to the heart, permitting heating of the stent and ultrasound wave penetration parameters to be more easily optimized. It can also be inserted between two ribs in the intercostal space so that the chance of bone reflection is minimized.

Another way of ultrasonically heating the implanted stent is to introduce an intravascular ultrasound (IVUS) transducer into the vessel lumen and to irradiate the stent from inside. This mode of treatment (which places the ultrasound source much closer to the stent than is possible with external procedures) might be preferred under certain circumstances, particularly if it can be combined with another invasive cardiovascular procedure.

In contrast to other ultrasound based heating methods, which are used primarily for thermal therapy of tumors or other large areas of tissue, the present method does not rely on direct absorbance of ultrasound waves by the tissue to achieve heating. Instead, the present method heats the tissue primarily by conduction of heat out of the ultrasonically heated stent coating material. The stent of the present invention is expected to be especially useful for gently heating small regions of vessel wall tissue, particularly vascular sites where a plaque has undergone angioplasty or atherectomy. This gentle, or low grade heating of vessel tissue closest to and surrounding the stent to 38–42° C. is accomplished as the coated stent experiences a 1–5° C. temperature rise above ambient vessel temperature due to the ultrasound irradiation. Other types of vessel wall conditions that might benefit from similar treatment include vasculitis of great vessels like Takayasu syndrome, which narrows the orifice of central arteries such as the common carotid and subclavian. It might also be applicable to patients with renal artery stenosis, which is the major cause of secondary hypertension in children and adolescence. Another possible application is treatment of a cancerous tumor by sealing the feeding artery using non-invasive focused ultrasound to heat only a plastic stent implanted inside the artery. In this case a plastic stent should be designed so as to melt and occlude or seal the artery, producing effects similar to thromboembolization of a tumor artery. One difference between the present method and conventional high intensity focused ultrasound techniques is that the latter method is intended to bum the whole tumor tissue. However, because it is not possible to clearly define the margin of a tumor, there is almost always some remnant.

By appropriately modifying the ultrasound heatable stents of the present invention, a similar treatment regimen can be applied to treat luminal cancer tissue such as bladder, neck, prostate, as well as intestinal lumen and billiary duct cancers. If temperatures higher than about 42° C. are required for a particular application, the choice and thickness of the ultrasound-absorptive coating material is merely modified. Greater heat generation is produced with thicker coatings having higher acoustic impedence characteristics and by reflection due to the presence of a higher-absorbing acoustic material. Of course the ultrasound-absorptive materials selected must also be chemically stable at the higher temperatures, such as those commonly employed for treatment of cancer and other pathophysiological conditions.

An alternative use of the ultrasonically heated stents of the invention for treating infected, or possibly infected stents to reduce or eliminate the infection. Another alternative application of the new US-sensitive coated stents is for performing non-invasive thrombolysis of endolumenal clots. In this embodiment, a focused ultrasound beam is directed obliquely onto the stent in such a way that the stent reflects ultrasound waves into the clot.

Ultrasonic Heating of a Synthetic Vascular Graft

Having established that materials with different acoustic impedances have corresponding differences in their rate of heating, and that these characteristics can be used to advantage to cause gentle or low grade heating of body tissue, the inventors will examine additional biocompatible polymers or plastics to identify therapeutically useful ones that are susceptible to ultrasonic heating. Oftentimes after implantation of a graft, such as an arterio-venus (AV) graft, inflammatory cells accumulate inside the graft lumen. This is due, at least in part, to the injury resulting from the surgery (implantation), and also to the fact that the graft, even though made of "biocompatible" material is still a foreign body which minimally stimulates immune cells. Also, in the case of AV grafts, because of the disturbed blood flow, it induces local intimal injury adjacent the graft where it meets the vein. Accumulation of inflammatory cells, overgrowth of vascular tissue, and clots leads to AV graft stenosis. A population of inflammatory cells is reduced or eliminated without invasive measures by applying external low intensity ultrasound to the graft. The ultrasound irradiation is such that the graft material becomes heated to a temperature in the range of 39–42° C., for example, for a period of time sufficient to induce apoptosis in the inflammatory cells.

Another type of synthetic graft that is subject to an influx of inflammatory cells and to blockage due to thrombus formation is the arterio-venous hemodialysis shunt. Since arteriovenous hemodialysis shunts are relatively superficially located, an ultrasound-heatable shunt is readily heated up using ultrasound diathermy. Ultrasound diathermy, similar to that used in physical therapy, provides 2–3 cm signal penetration, which is adequate to warm an arterio-venous hemodialysis shunt made of suitable ultrasound sensitive material by 1–5° C., at least. As is the case with endolumenal stents, described above, inflammatory cells that have migrated into the hemodialysis shunt are reduced or eliminated by the heat treatment.

Use of the Ultrasonically Heatable Stent for Periodic Local Drug Delivery

In some treatment modalities it would be beneficial to have a drug entrapped by a heat sensitive, ultrasound heatable polymer coating on a stent, or other implanted medical device. With such a coated device, measured aliquots of a drug could be released as desired by directing an external ultrasound source toward the stent, or other device, to heat the coating and release the drug. A drug, such as an anti-inflammatory drug, is incorporated into the matrix of a polymer-coated stent for periodic release at a stent implantation site by action of an external ultrasonic trigger. The coating material is a US-heatable polymer that releases a portion of the drug upon being heated to a threshold temperature, whereby the permeability of the polymer increases and a quantity of the drug is released at the stented region of the vessel wall. Once the ultrasound is turned off and the temperature of the device is allowed to return to ambient body temperature, the polymer returns to its less drug permeable state. As needed, the stent can later on be heated again, via ultrasound, to release additional drug.

Alternatively, the drug of interest is contained in heat-sensitive liposomes that are injected into the blood stream. Upon heating the stent ultrasonically, as described above, the drug is released from the liposomes as they reach the "hot spot" in the vessel constituting the stent location. In this case, the area of interest for drug delivery can be downstream of the artery or the whole heart muscle. Stent heating is of short enough duration that significant heating of the blood is not produced.

While preferred embodiments of the invention have been shown and described, modifications thereof can be made by one skilled in the art without departing from the spirit and teachings of the invention. The embodiments described herein are exemplary only, and are not limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

REFERENCES CITED

The following references to the extent that they provide procedural details supplementary to those set forth herein, are specifically incorporated herein by reference.

Barnett et al. *Med. J. Aust.* 1994; 160:33–37.
Barnett S. ed. *Ultrasound in Medicine and Biology* 1998; 24: Supp 1:S1–S57.
Belli J A and Bonte F J. Influence of temperature on the radiation response of mammalian cells in tissue culture. *Radiat. Res.* 1963;18:272–6.
Berliner J A, Navab M, Fogelman A M, Frank J S, Demer L L, Edwards P A, Watson A D, Lusis A J. Atherosclerosis: basic mechanisms. Oxidation, inflammation, and genetics. *Circulation* 1995;91:2488–2496.
Biffl W L, Moore E E, Moore F A, Barnett C C, Jr., Carl V S, Peterson V N. Interleukin-6 delays neutrophil apoptosis. *Archives of Surgery* 1996;131(1):24–9; discussion 29–30.
Blackburn M J, Wheldon T E, Field S B, Goldman J M. The sensitivity to hyperthermia of human granulocyte/macrophage progenitor cells (CDU-GM derived from blood or marrow of normal subjects and patients with chronic granulocytic leukaemia. *British J. of Cancer* 1984;506:745–51.
Buja L, Willerson J T, Roll of Inflammation in Coronary Plaque Disruption. (1994) *Circulation* 89, 2303–5.
Casscells W, Engler D, Willerson J T, Mechanisms of Restenosis, *Texas Heart Inst. J.* (1994) 21: 68–77.
Chen B D, Sapareto S A, Chou T H. Induction of prostaglandin production by hyperthermia in murine peritoneal exudate macrophages. *Cancer Res.* 1987;37(1):11–15.
Cohen D S, Palmer E, Welch W J, Sheppard D. The response of guinea pig airway epithelial cells and alveolar macrophages to environmental stress. *Am. HJ Resp. Cells and Molec. Bio.* 1991;5(2):133–43.
Elkon D, McOrath H E. Thermal inactivation energy of granulocyte-monocyte stem cells. *Radiat. Res.,* 1981;87:367–72.

Ensor J E, Crawford E K, Hasday J D. Warming macrophages to febrile range destabilized tumor necrosis factor-a MRNA without inducing heat shock. *Am. J. Physiol* 269 (*Cell Physiol.*38) 1995:C1140–C1146.

Falk E, Shah P K, Fuster V, Coronary Plaque Disruption. *Circulation* 1995, 92 157–71.

Fan, Hynynen. *J. Acoust. Soc. Am.* 1992; 91:1727–36.

Field S B, Morris C C. The relationship between heating time and temperature: its relevance to clinical hyperthermia. *Radiotherapy & Oncology* 1983;1:179–186.

Fouqueray B, Phillipe C, Amrani A, Perez J, Baud L. Heat shock prevents lipopolysaccharide-induced tumor necrosis factor-alpha synthesis by rat mononuclear phagocytes. *Europ. J. Immunol.* 1992;22(11):2983–7.

Freeman M L, Raaphorst G P, Hopwood L E, Dewey W C. The effect of pH on cell lethality induced by hyperthermia treatment. *Cancer* 1980;45:2791–2300.

Gerweck L E, Dahlberg W K, Epstein L F, Shimm D S. Influence of nutrient and energy deprivation on cellular response to single and fractionated heat treatments. *Radiat. Res.* 1984;99:573–81.

Goldberg et al. *J. Vasc. Interv. Radiol.* 1997; 8:835–43.

Hamilton R F Jr., Li L, Felder T B, Holian A. Bleomycin induces apoptosis in human alveolar macrophages. *Amer. J. Physiol.* 1995;269(3, Pt. 1):L318–25.

Haveman J, Hahn G M. The role of energy in hyperthermia-induced mammalian cell inactivation: a study of the effects of glucose starvation and an uncoupler of oxidative phosphorylation. *J. Cellular Physiol* 1982;107:237–241.

Katsuda, S. Human Atherosclerosis. *Amer. J. Path.* 1993;142:1787–93.

Kim Y M, de Vera M E, Watkins S C, Billiar T R. Nitric oxide protects cultured rat hepatocytes from tumor necrosis factor-alpha-induced apoptosis by inducing heat shock protein 70 expression. *J. Biological Chem.* 1997;272(2):1402–11.

Kimura et al. J. Orthop. Sports Phys. Ther. 1998; 1:27–31.

Klostergaard J, Bara M, Tomasovic S P. Hyperthermic modulation of tumor necrosis factor dependent, *Cancer Res.* 1989; 49: 6257–7.

Kobayashi E, Yamagishi M, Kamamoto Y, Yoshida Y, Uchino H. Cell cycle-dependent heat sensitization of murine granulocyte-macrophage progenitor cells in regenerating marrow. *Cancer Res.* 1985;45(4):1459–63.

Kunkel S L, Wiggins E C, Chensue S W, Larrick J. *Biochem. Biophys. Res. Comm.* 1986;137:404–10.

Lavie L, Weinreb O, Gershon D. Age-related alterations in superoxide anion generation in mouse peritoneal macrophages studied by repeated stimulations and heat shock treatment. *J Cellular Physio.* 1992;152(2):382–8.

Luo et al. *Thrombosis Research* 1998; 89:171–177.

Mangan D F, Welch G R, Wahl S M. Lipopolysaccharide tumor necrosis factor alpha and IL-1 prevent programmed cell death (apoptosis) in human peripheral blood monocytes. *J. Immunol.* 1991;146:1541–46.

McDiarmid, et al. Clinical Applications of Therapeutic Ultrasound. *Physiotherapy* 1987; March/April: 14–21.

Morange M, Dubois M F F, Bensaude O, Lebou P. Interferon pretreatment lowers the threshold for maximal heat-shock response. *J. Cell Physiol.* 1986;127:417-.

Moreno P R, Fallon J., Shah P, Fuster V, Restenosis and Thrombosis Formation related to Macrophage Migration.

S. Nagata, P. Golstein, The Fas death factor. *Science* 1995;267:1449–1455.

Nishina H, Fischer K D, Radvanyi L, Shahinian A, Hakem R, Rubie E A, Bernstein A, Mak T W, Woodgett J R, Penninger J M. Stress-signaling kinase Seki protects thymocytes from apoptosis mediated by CD95 and CD3. *Nature* 1997;385 (6614):350–3.

O'Hara M D, Xiong Q B, Boyer J W, Leeper D B. Intrinsic Thermal response, thermotolerance development and stepdown heating in murine bone marrow progenitor cells. *International J Hyperthermia* 1992;8(4):451–61.

Oesterle et al. *Am. Heart J.* 1998; 136:578–599.

Papadimitriou J M, van Bruggen I. Quantitative investigations of apoptosis of murine mononuclear phagocytes during mild hyperthermia. *Experimental & Molecular Pathol.* 1993;59(1):1–12.

Pizurk L, Polla B S. *J. Cell Physiol.* 1994; 161:169–77.

Prins J B, Walker N I, Winterford C M, Cameron D P. Apoptosis of human adipocytes in vitro. *Biochemical and Biophysical Res. Comm.* 1994;201(2):500–7.

Raaphorst G P, Broski A P, Azzam E I. Sensitivity to heat, radiation and heat Plus radiation of Chinese hamster cells synchronized by mitotic selection, thymidine block or hydroxyurea block. *J. Therm. Biol.* 1986;10(3):177–181.

Reddy M V, Gangadharam P R. Heat shock treatment of macrophages causes increased release of superoxide anion. *Infection & Immunity* 1992;60(6):2386–90.

Ribeiro S P, Villar J, Downey G P, Edelson J E, Slutsky A S. Effects of the stress response in septic rats and LPS-stimulated alveolar macrophages: evidence for TNO-alpha posttranslation regulation. *Am. J. of Resp. and Critical Care Med* 1996;154(6 Pt 1):1843–50.

Robertson et al. *Arch. Phys. Med. Rehab.* 1995; 76:569–75.

Ross R., The Pathogenisis of Atherosclerosis, *Nature* 1993, 362, 801–9.

Sivo J, Harmon J M, Vogen S N. Heat shock mimics glucocorticoid effects on IFN-gamma-induced Fc gamma RI and Ia messenger RNA expression in mouse peritoneal macrophages. *J Immunol.* 1996;156(9):3450–4.

Snyder Y M, Guthrie L, Evans G F, Zuckerman S H. Transcriptional inhibition of endotoxin-induced monokine synthesis following heat shock in murine peritoneal macrophages. *J Leukocyte Biol.* 1992;51(2):181–7.

Steller H, Mechanisms and genes of cellular suicide. *Science* 1995;267: 1445–1449.

Thompson C B, Apoptosis in the pathogenesis and treatment of disease. *Science* 1995;267: 1456–1462.

Topol et al. *Circulation* 1998; 98:1802–1820.

Vaux D L, Strasser A, The molecular biology of apoptosis, *PNAS*(USA) 1996;93 :2239–2244

Verhelj M, Bose R, Xin X L, Yao B, Jarvis W D, Grant S, Birrer M J, Szolo E, Zon L I, Kynakis J M, Haimoritz-Friedman A, Furks Z, Kolesnik R N. Requirement for ceramide-initiated SAPKIJNK signalling in stress-induced apoptosis. *Nature* 1996;380:75–9.

Wang J H, Redmond H P Watson R W, Condron C, Bouchier-Hayes D. Induction of heat shock protein 72 prevents neutrophil-mediated human endothelial cell necrosis. *Archives of Surg* 1995;130(12):1260–5.

Wang J H, Redmond H P, Watson R W, Bouchier-Hayes D. Induction of human endothelial cell apoptosis required both heat shock and oxidative stress responses. *Amer. J. Physiol.* 1997;272(5Pt 1):C1543–51.

Wells P., ed. *Ultrasound in Medicine and Biology* 1992; 18:739–811.

Westra A and Dewey W C. Variation in sensitivity to heat shock during the cell cycle of Chinese hamster cells in vitro. *International J. Radiat. Biol.* 1971;19:467–77.

Wike-Hooly, Haveman J, Reinhold H S. The relevance of tumor pH to the treatment of malignant disease. *Radiotherapy & Oncology* 1984;2:343–66.

William R, Watson G, Redmond H P, Wang J H, Bouchier-Hayes D. Bacterial ingestion, tumor necrosis factor-alpha, and heat induced programmed cell death in activated neutrophils. *Shock* 1996;5(1):47–51.

Williams R. Production and Transmission of Ultrasound. *Physiotherapy* 1987; March/April 5–7.

What is claimed is:

1. An ultrasonically heatable stent comprising at least one ultrasound-absorptive material characterized by an acoustic impedance greater than that of living soft tissue.

2. The stent of claim 1 further comprising:
a stent framework configured to maintain patency of a human vessel, and
a coating comprising said at least one ultrasound-absorptive material overlying said stent framework and characterized by being heatable by ultrasound at a faster rate than living soft tissue.

3. The stent of claim 2 wherein said stent framework is wire mesh.

4. The stent of claim 2 wherein said at least one ultrasound-absorptive material has a heating rate greater than 0.86° C. per minute when subjected to an ultrasound beam of 1 mHz frequency and 1 Watt/cm$^2$ intensity.

5. The stent of claim 2 wherein said coating further comprises a heat-releasable drug.

6. The stent of claim 2 wherein said coating comprises at least two ultrasound-absorptive layers, one said layer overlying at least one other layer, said layers having dissimilar acoustic impedance characteristics and together enhancing the ultrasound-induced temperature increase of said stent when exposed to ultrasound.

7. The stent of claim 2 wherein said coating is characterized by a temperature increase of 1–5° C. in response to ultrasound irradiation.

8. The stent of claim 2 wherein said stent is configured to contact a region of vessel wall, and said coating is further characterized by having an acoustic impedance greater than that of any intervening tissue between said stent and an external ultrasound transducer, when said stent is situated in a vessel and ultrasonic radiation is directed onto said stent.

9. The stent of claim 1 wherein said at least one material is a polymer.

10. The stent of claim 9 wherein said polymer is chosen from the group consisting of silicone, polyvinylchloride, polyurethane, nylon, phosphorylcholine and combinations thereof.

11. A method of making an ultrasonically heatable stent comprising:
obtaining a stent framework configured for maintaining patency of a vessel;
obtaining a biocompatible coating material characterized by having an acoustic impedance greater than that of human soft tissue;
applying a coating of said material to said stent framework, said coating being of such thickness and character that said stent is heatable by ultrasound at a faster rate than human soft tissue.

12. The method of claim 11 wherein said obtaining a biocompatible coating material comprises choosing a material from the group consisting of silicone, nylon, polyvinylchloride, polyurethane, phosphorylcholine, and combinations thereof.

13. The method of claim 11 wherein said step of obtaining a biocompatible coating material includes choosing a material having a heating rate greater than 0.86° C. per minute when subjected to an ultrasound beam of 1 mHz frequency and 1 Watt/cm$^2$ intensity.

14. The method of claim 11 wherein said step of applying a coating of said material to said stent framework comprises applying at least two layers of coating material, each said layer chosen from the group of materials consisting of silicone, polyvinylchloride, nylon, polyurethane, phosphorylcholine, and combinations thereof, said coating being of such thickness and character that said stent is heatable by ultrasound at a faster rate than human soft tissue whereby a temperature about 1–5° C. above ambient temperature is induced in said stent.

15. A method of treating an atherosclerotic plaque in a living subject comprising:
obtaining the ultrasonically heatable stent of claim 1;
positioning said stent in a vessel lumen so as to contact a region of vessel wall comprising an atherosclerotic plaque;
advantageously positioning at least one ultrasound transducer external the body of said subject; and
operating said ultrasound transducer such that an ultrasonic beam is directed at said stent, whereby the temperature of said stent is maintained at about 1–5° C. above ambient temperature for a sufficient period of time to heat said region of vessel wall at a temperature of 38–42° C.

16. The method of claim 15 further comprising:
measuring the temperature of said region of vessel wall; and
employing a microprocessor and visual display system to control the operation of said ultrasound transducer and to receive, analyze and display said temperature measurements.

17. The method of claim 15 wherein said ultrasonic beam is directed using an acoustic lens to focus the ultrasound beam.

18. The method of claim 15 wherein two or more ultrasound transducers are advantageously positioned external the body of said subject and wherein said ultrasound transducers are operated in cooperation such that at least two ultrasonic beams are directed at said stent.

19. The method of claim 15 wherein said step of advantageously positioning an ultrasound transducer external the body of said subject is omitted and the step of positioning at least one transducer inside the esophagus.

20. The method of claim 15 wherein said step of advantageously positioning an ultrasound transducer external the body of said subject is omitted and the step of positioning an intravascular ultrasound transducer inside said stent is substituted therefor.

21. A method of treating a vascular injury comprising:
obtaining the ultrasonically heatable stent of claim 1;
positioning said stent in a vessel lumen so as to contact a region of vessel wall comprising an endoluminal vascular injury in need of treatment;
advantageously positioning an ultrasound transducer inside said stent; and
operating said ultrasound transducer such that an ultrasonic beam is directed at said stent, whereby the temperature of said stent is maintained at about 1–5° C. above ambient temperature for a sufficient period of time to heat said region of vessel wall at a temperature of 39–40° C.

22. The method of claim 21 wherein said step of positioning said stent in a vessel lumen comprises positioning said stent at an angioplasty or atherectomy site.

23. The method of claim 21 further comprising:
subsequent to said 39–40° C. maintaining step, detecting restriction of blood flow through said stent; and operating said ultrasound transducer such that an ultrasonic beam is directed onto said stent, whereby the temperature of said stent is maintained at a temperature about 1–5° C. above ambient temperature for a sufficient period of time to heat said region of vessel wall at 42° C. for 15–30 minutes.

24. A method of reducing or eliminating a population of inflammatory cells on an implanted synthetic vascular graft in a living subject comprising:

advantageously positioning an ultrasound transducer external the body of said subject; and operating said ultrasound transducer such that an ultrasonic beam is directed at said synthetic vascular graft, whereby the temperature of the graft, or a portion thereof, is increased to and maintained at about 1–5° C. above ambient vessel temperature for a sufficient period of time to heat said graft or portion thereof at a temperature of 38–42° C., provided that said synthetic graft contains an ultrasound-absorptive material characterized by an acoustic impedance greater than that of human tissue and that is chemically stable when heated up to about 45° C.

25. A method of inhibiting or regressing in-stent restenosis comprising:

implanting the ultrasonically heatable stent of claim 1 into a vessel of a subject;

advantageously positioning an ultrasound transducer external the body of said subject; and operating said ultrasound transducer such that an ultrasonic beam is directed at said stent, whereby the temperature of the stent is increased to and maintained at about 1–5° C. above ambient vessel temperature for a sufficient period of time to heat said stent at a temperature of 41–42° C.

26. An ultrasonically heatable stent comprising at least one ultrasound-absorptive material characterized by an acoustic impedance greater than that of living soft tissue;

said stent comprising a stent framework configured to maintain patency of a human vessel; and a coating comprising said at least one ultrasound-absorptive material overlying said stent framework and characterized by being heatable by ultrasound at a faster rate than living soft tissue.

27. An ultrasonically heatable stent comprising at least one ultrasound-absorptive material characterized by an acoustic impedance greater than that of living soft tissue;

said stent comprising:

a stent framework configured to maintain patency of a human vessel, and a coating comprising said at least one ultrasound-absorptive material overlying said stent framework and characterized by being heatable by ultrasound at a faster rate than living soft tissue;

wherein said coating further comprises a heat-releasable drug.

28. The stent of claim 27 wherein said coating further comprises an ultrasonically heatable polymeric matrix and said heat-releasable drug is incorporated into the said polymeric matrix.

29. A method of delivering a drug to a site in vivo, comprising the steps of:

incorporating the drug into an ultrasonically heatable polymeric coating of a stent;

delivering the coated stent to a specific region in vivo; and directing an external ultrasound source toward the stent, thereby heating the coating and releasing the drug.

* * * * *